United States Patent
Beckett et al.

(10) Patent No.: US 6,740,333 B2
(45) Date of Patent: May 25, 2004

(54) SUPPOSITORY AND COMPOSITION COMPRISING AT LEAST ONE POLYETHYLENE GLYCOL

(75) Inventors: Christian Westy Beckett, Aalsgaarde (DK); Per Robert Topp Eliasen, Koersoer (DK)

(73) Assignee: Anestic ApS, Aalsgaarde (DK)

( * ) Notice: Subject to any disclaimer, the term of this patent is extended or adjusted under 35 U.S.C. 154(b) by 0 days.

(21) Appl. No.: 09/899,567

(22) Filed: Jul. 6, 2001

(65) Prior Publication Data

US 2002/0048601 A1 Apr. 25, 2002

Related U.S. Application Data

(60) Provisional application No. 60/256,923, filed on Dec. 21, 2000.

(30) Foreign Application Priority Data

Jul. 7, 2000 (DK) .......................................... 200001067
Dec. 21, 2000 (DK) .......................................... 200001923
Jul. 3, 2001 (DK) .......................................... 200101050

(51) Int. Cl.$^7$ .................................................. A61F 9/02
(52) U.S. Cl. .................................. 424/436; 424/DIG. 5; 514/965; 514/966
(58) Field of Search .................... 424/436, DIG. 15; 514/965, 966

(56) References Cited

PUBLICATIONS

Noriaki Ohnishi et al, Evaluation of Indomethecin Sustained–Release Suppositories Prepared with a Methacrylic Acid––Methacrylic Methyl Ester Copolymer–Polyethylene Glycol 2000 Solid Matrix, Chem. Phar. Bull., 1988, 36:430–434.*

(List continued on next page.)

Primary Examiner—Carlos A. Azpuru
(74) Attorney, Agent, or Firm—Iver P. Cooper

(57) ABSTRACT

There is provided a suppository comprising at least one biocompatible polymer, wherein the biocompatible polymer is essentially non-biodegradable, and wherein the suppository essentially does not swell when contacted with an aqueous fluid. The suppository may further comprise a plurality of open cells at least partly separated from one another by an interpenetrating matrix comprising at least one biocompatible polymer in branched or crosslinked form. The plurality of interlinked, open cells are capable of containing an aqueous fluid, and the permeability of the suppository ensures that entry of body fluids into the open cells under practical circumstances occurs essentially without dehydration of mucousal membrane tissue contacting the suppository. The suppository furthermore preferably comprises a controlled release formulation.

155 Claims, 6 Drawing Sheets-

OTHER PUBLICATIONS

J56040608–A, Long lasting compositions for rectal administration—comprises a microencapsulated active ingredient and at least one oil base.

CN 1109347 A, Anti–inflammatory sponginum.

CA 2,286,225, Sengupta et al., Adherent microcapsules containing biologicallyl active ingredients.

GB 2,150,938, Gould et al., Hydrophilic polyurethane acrylate compositions.

Thorlakson et al., Pain and bleeding after anorectal operations with special reference to anal dressings, *Surgery, Gynecology & Obstetics*, Jul. 1963, 56–60.

U.S. patent application Ser. No. 3,356,650, McElroy, Thermoplastic polyurethanes.

U.S. patent application Ser. No. 4,062,826, Hutchinson et al., Polymeric shaped articles.

U.S. patent application Ser. No. 4,259,314, Lowey, Method and composition for the preparation of controlled long–acting pharmaceuticals.

U.S. patent application Ser. No. 4,292,299, Suzuki et al., Slow–releasing medical preparation to be administered by adhering to a wet mucous surface.

U.S. patent application Ser. No. 4,292,300, Byrne et al., Controlled release suppositories.

U.S. patent application Ser. No. 4,393,871, Vorhauer et al., Vaginal device.

U.S. patent application Ser. No. 4,402,692, Takagishi et al., Medicament capsules for rectal application.

U.S. patent application Ser. No. 4,404,296, Schäpel, Gel compositons with depot action based on a polyurethane matrix and relatively high molecular weight polyols and containing active ingredients, and a process for their preparation.

U.S. patent application Ser. No. 4,406,883, Byrne et al., Controlled release suppositories consisting essentially of a linear polymer particularly, polyvinyl pyrrolidones.

U.S. patent application Ser. No. 4,564,362, Burnhill et al., Vaginal device.

U.S. patent application Ser. No. 4,594,380, Chapin et al., Elastomeric controlled release formulation and article comprising the same.

U.S. patent application Ser. No. 4,601,714, Burnhill et al., Vaginal device.

U.S. patent application Ser. No. 4,659,696, Hirai et al., Pharmaceutical composition and its nasal or vaginal use.

U.S. patent application Ser. No. 4,698,359, Niederer et al., Medicated suppositorie.

U.S. patent application Ser. No. 4,765,978, Abidi et al., Novel vaginal suppository.

U.S. patent application Ser. No. 4,767,812, Chapin et al., Article comprising an elastomeric controlled release insecticide.

U.S. patent application Ser. No. 4,769,435, Lunardon et al., Process for the manifacture of thermoplastic polyurethanes.

U.S. patent application Ser. No. 4,786,502, Chapura et al., Palatable solid pharmaceutical compositions.

U.S. patent application Ser. No. 4,795,643, Seth et al., Medicament with a delayed release of active ingredient.

U.S. patent application Ser. No. 4,853,211, Kurobe et al., Stable, effervescent vaginal suppositories.

U.S. patent application Ser. No. 4,954,298, Yamamoto et al., Method for producing microcapsule.

U.S. patent application Ser. No. 4,981,465, Ballan et al., Disposable closure means for an artificial ostomy opening or an incontinent natural anus.

U.S. patent application Ser. No. 4,999,342, Ahmad et al., Long lasting contraceptive suppository composition and methods of use.

U.S. patent application Ser. No. 5,032,622, Herrington et al., Densifiable and re–expandable polyurethane foam.

U.S. patent application Ser. No. 5,044,376, Shields, Vaginal diaphragms with medicament dispensing foam pads.

U.S. patent application Ser. No. 5,081,210, Sarpeshkar et al., Polyurethane elastomers.

U.S. patent application Ser. No. 5,085,650, Giglio et al., Gynecological urethral suppository.

U.S. patent application Ser. No. 5,180,392, Skeie et al., Anastomotic device.

U.S. patent application Ser. No. 5,213,808, Bar–Shalom et al., Controlled release article with pulsatile release.

U.S. patent application Ser. No. 5,330,427, Weissenburger et al., Prefilled suppository applicator.

U.S. patent application Ser. No. 5,411,737, Hsu et al., Slow release syneresing polymeric drug delivery device.

U.S. patent application Ser. No. 5,436,009, Jauw et al,. Sustained release suppositories and a process for preparation.

U.S. patent application Ser. No. 5,512,055, Domb et al., Anti–infective and anti–inflammatory releasing systems for medical devices.

U.S. patent application Ser. No. 5,527,534, Myhling, Vaginal sponge delivery system.

U.S. patent application Ser. No. 5,529,782, Staab, Dissolvable device contraception or delivery of medication.

U.S. patent application Ser. No. 5,618,560, Bar–Shalom et al., Controlled release erodible composition.

U.S. patent application Ser. No. 5,750,100, Yamagata et al., Sustained releaseable parenteral pharmaceutical preparations and method of producing the same.

U.S. patent application Ser. No. 5,814,329, Shah et al., Hydrophilic polystyrene graft copolymer vehicle for intravaginal administration of pharmacologically active agents.

U.S. patent application Ser. No. 5,830,186, Gonzales et al., Method of dispensing medications by use of mucous membrane infusor.

U.S. patent application Ser. No. 5,833,665, Bootman et al., Polyurethane–biopolymer composite.

U.S. patent application Ser. No. 5,846,216, Gonzales et al., Mucous membrane infusor and method of use for dispensing medications.

U.S. patent application Ser. No. 5,859,048, Oohashi et al., Pharmaceutics for mucosal adminstration.

U.S. patent application Ser. No. 5,900,442, Leenslag et al., Flexible polyurethane foams.

U.S. patent application Ser. No. 6,020,390, Leenslag et al., Process for making flexible polyurethane foams.

U.S. patent application Ser. No. 6,020,391, Leenslag et al., Flexible polyurethane foams.

U.S. patent application Ser. No. 6,034,149, Bleys et al., Hydrophilic polyurethane foams.

U.S. patent application Ser. No. 6,043,292, Huygens et al., Process for making flexible polyurethane foams.

U.S. patent application Ser. No. 6,180,129, Magruder et al., Polyurethane–containing delivery systems.

U.S. patent application Ser. No. 6,238,687, Mao et al., Biodegradable polymers, compositions, articles and methods for making and using the same.

U.S. patent application Ser. No. 6,200,590, Eley, Controlled, phase–release suppository and its method of production–Mar. 13, 2001.

U.S. patent application Ser. No. 4,959,217, Sanders et al., Delayed/sustained release of macromolecules–Sep. 25, 1990.

U.S. patent application Ser. No. 4,292,300, Byrne et al., Controlled release suppositories–Sep. 29, 1981.

Nilüfer Tarimci et al., Preparation and in vitro evaluation of sustained release suppositories of Indomethacine, J. Fac. Pharm. Ankara, 1998, 27:11–21.

Dilek Ermis et al., ketoprofen sustained–released suppositories containing hydroxypropylmethylcellulose phyhalate in polyethylene glycol bases, Int. J. Pharmaceutics, 1995, 113:65–71.

Noriaki Ohnishi et al., Evaluation of Indomethacin sustained–release suppositories prepared with a methacrylic acid–methacrylic methyl ester copolymer–polyethylene glycol 2000 solid matrix, Chem. Phar. Bull., 1988, 36:430–434.

Ian W. Kellaway et al., Correlations between physical and drug release characteristics of polyethylene glycol suppositories, J. Pharm. Sci., 1975, 64: 1162–1166.

JP 7 100191, Daikyo Yakuhin Kogyo KK, Release–controlled suppository for treatment of e.g. angina pectoris, coronary diseases, myocardial infarction etc., comprises Witpsol and EVAc copolymer mixt. ethylene glycol and vepramil hydrochloride (abstract)–Apr. 18, 1995.

JP 6 1236723, Fujimoto Seiyaku KK, Sustained release nifedipine suppository–contains polyethylene glycol base material and polymer e.g. polyvinyl pyrrolidone or polyvinyl alcohol (abstract)–Oct. 22, 1986.

JP 5 6040608, Nippon Chemiphar Co, Long lasting compositions for rectal administration—comprises a microencapsulated active ingredient and at least one oil base (abstract)–Apr. 16, 1981.

JP 6 040889, Koyama Y, New high dispersibility stable, sustained release suppository—comprises acrylic acid, polyvinyl pyrrolidone and oily suppository base (abstract)–Feb. 15, 1994.

JP 5 6142208, Ono Pharm Co ltd, Vaginal suppostitories containing protaglandins—include water–soluble and water– insoluble high molecular weight compounds, plasticiser and organic acid. (abstract)–Nov. 6, 1981.

* cited by examiner

SUPPOSITORY AND COMPOSITION COMPRISING AT LEAST ONE POLYETHYLENE GLYCOL

The present application claims the benefit of U.S. Provisional Application No. 60/256,923, filed Dec. 21, 2000, hereby incorporated by reference in its entirety. It also claims the benefit of Danish applications PA 2000 01067 (Jul. 7, 2000), PA 2000 01923 (Dec. 21, 2000), and PA 2001 01050 (Jul 3, 2001), also incorporated by reference in their entirety. Finally, all patents, patent applications and publications cited herein are incorporated by reference in their entirety.

TECHNICAL FIELD

The present invention relates to a composition comprising a biocompatible polymer and specially adapted for forming at least part of a suppository. The composition preferably comprises a medicament.

BACKGROUND OF THE INVENTION

CN 1109347 concerns a suppository made from a polyurethane sponge. The sponge in the shape of a suppository is dipped into a solution of the medicament to absorb it and is subsequently dried.

U.S. Pat. No. 4,292,300 relates to a non-dissolving, non-disintegrating slow-release suppository base consisting essentially of a linear polymer, such as methyl cellulose, and water in an amount of more than 35 parts by weight and less than 65 parts by weight of linear polymer. The linear polymers according to U.S. Pat. No. 4,292,300 can be distinguished from cross-linked polymers which swell, but do not dissolve in the presence of water and certain organic solvents. The linear polymers according to U.S. Pat. No. 4,292,300 have a high molecular weight, an affinity for water, and will dissolve in excess water, but in the relatively small amounts of water used in the formulation according to U.S. Pat. No. 4,292,300, a "gel"-like mass is formed. The linear polymers preferably resist biodegradation, or they are only slowly biodegradable. The polymers are capable of being extruded at ambient or near ambient temperatures, e.g. from 15° C. to 40° C., to give products with good strength and elasticity. They also have the ability to become instantaneously slippery when only slightly moistened and are therefore easily inserted into the anorectal or vaginal passage, this property is enhanced by the presence of the relatively large amounts of water in the formulations according to U.S. Pat. No. 4,292,300. Examples of linear polymers are methylcellulose, hydroxyproplymethylcellulose, hydroxymethylcellulose, polyvinyl alcohols, polyvinyl pyrrolidones, polyacrylamides, polyethylene oxides and certain modified starches. Typical average molecular weights vary between 100,000 and 300,000.

U.S. Pat. No. 4,405,883 relates to a non-dissolving, non-disintegrating, slow-release, shaped suppository consisting essentially of polyvinyl pyrrolidone, water, and a therapeutically effective amount of a water-soluble therapeutically active ingredient, wherein the water is present in an amount of more than 35 parts by weight wherein the suppository has flexibility and becomes slippery when moistened, U.S. Pat. No. 5,330,427 relates to an improved suppository applicator which is a one-piece injection molded suppository applicator for ejecting medicament into a body cavity comprising a cylindrical main body portion having a distal end and a proximal end. The main body portion further comprises: an integral flexible chamber means at the distal end; a flexible junction means adjacent, integral to and at least partially the flexible chamber means; a plunger means adjacent and integral to the flexible chamber means; and a barrel stem; wherein the flexible junction means integrally joins the plunger means and flexible chamber means within the barrel stem.

U.S. Pat. No. 4,292,299 relates to a medical preparation composed of an adhesive layer comprising polymers which have adhesiveness to a wet mucous surface and swellability upon moistening and a nonadhesive layer which has no adhesiveness to a wet mucous surface and is water soluble or water disintegrable, with at least one of the layers made to contain a medicament. The medical preparation is administered by adhering to a wet mucous surface of the mucousal membrane and skin of men or animals, wherein exhibiting a property to release the medicament slowly extending over a long period of time to cure or prevent general or local diseases.

U.S. Pat. No. 4,404,296 relates to a polyol gel comprising i) 15-62 weight % (based on i)+ii)) of a high molecular weight covalently cross-linked polyurethane matrix; ii) 85–38 weight % (based on i)+ii)) of a liquid dispersing agent which is firmly bonded in the matrix by secondary valence forces; and optionally iii) fibers and/or additives and/or catalysts suitable for an isocyanate polyaddition reaction and/or active ingredients.

U.S. Pat. No. 5,411,737 relates to a slow release drug delivery device for the prolonged administration of topically active medicines which consists of a vehicle in which water is soluble. In the vehicle is dissolved a topically active drug formed into a stable organogel with a polymer matrix with a very low water absorbing capability. The organogel, in the presence of water or atmospheric water vapor, slowly imbibes such water into the vehicle and by doing so the vehicle becomes incompatible with the matrix and is slowly expelled therefrom. The vehicle dissolves the drug and the vehicle/drug combination is slowly pumped out of the polymeric matrix with substantially linear drug delivery occurring for periods in excess of 6 months. The drug delivery device may be used to administer drugs topically, such as a suppository or a subcutaneous implant.

U.S. Pat. No. 5,085,650 relates to a urethral suppository comprising i) a relatively long, relatively small diameter shaft, ii) a bulbous head extending from a rounded nose through a relatively gradually outwardly curving insertion surface having an axial length equaling about two thirds of the overall length of the head and a relatively sharply curving retention surface extending from the intersection with the insertion surface which is the maximum diameter of the head to an intersection with the shaft, the intersection between the retention surface and the insertion surface not comprising a sharp edge or corner, and iii) a conical tail including an outwardly tapered retaining surface extending from the shaft to a base having a diameter substantially greater than the maximum diameter of the bulbous head, wherein said shaft, head, and tail comprises predetermined dimensions and a unitary structure and are formed entirely from a medicament U.S. Pat. No. 4,999,342 relates to a long lasting, viscous, adhesive contraceptive made from a quick melting suppository composition and comprising a mixture of a contraceptive effective amount of a spermicidal agent; a polymeric gum, such as a polysaccharide gum; a dispersing agent comprising silica; and a water miscible polymer suppository base, such as polyethylene glycol.

U.S. Pat. No. 4,765,978 relates to an antifungal vaginal suppository which contain cis-2-(1H-imidazolylmethyl)-3-

(2',6'-difluorobenzyloxy)-2,3-dihydro-5-fluo robenzo[b] thiophene as the antifungal agent, in a suppository base containing biocompatible polymers, a surfactant and an absorbent in a vegetable oil phase. The suppositories are substantive and provide a prolonged duration of effectiveness. The biocompatible polymer component of the suppository formulation comprises a combination of polyethylene and polyvinylpyrrolidione.

U.S. Pat. No. 5,750,100 relates to a sustained releasable parenteral pharmaceutical preparation in which a great release of a physiologically active peptide or protein in an early stage of the administration is suppressed and the peptide or protein can be released for a longer period. The sustained releasable parenteral pharmaceutical preparation of the present invention comprises a matrix comprising a physiologically active peptide or protein and a polyglycerol diester of a saturated fatty acid. The matrix may be in a pillar, granular or other form.

U.S. Pat. No. 4,259,314 relates to a controlled release, dry pharmaceutical composition containing a dry carrier comprised of 80 to 95% of hydroxypropyl methylcellulose and 20 to 5% of hydroxypropyl cellulose. The carrier is dried to a moisture content of not more than 1%. If the pharmaceutical composition is compressed under low pressure, a troche capable of being sucked or used in the mouth can be prepared, and a controlled release of the active therapeutic agent, which is mucousally absorbed into the blood stream is achieved. If higher pressures are used to compress the pharmaceutical material a harder and longer-lasting pharmaceutical composition can be prepared suitable for rectal or vaginal application or suitable for swallowing in the form of a tablet.

U.S. Pat. No. 4,786,502 relates to a lipid-containing, molded pharmaceutical composition comprising i) from about 10% to about 50% of a lipid material having a melting point of from about 26° C. to about 37° C., ii) from about 10% to about 50% of a particulate dispersant material, iii) from about 0.1% to about 3% of an emulsifier, and iv) a safe and effective amount of a pharmaceutically active material, wherein preferably the measured. Viscosity of the composition is less than about 10,000 cps at about 40° C.

U.S. Pat. No. 5,529,782 relates to a dissolvable element containing an agent material that is used for local administration of an agent material in an internal body area. The dissolvable element is made of a dissolvable polymer material and/or complex carbohydrate material which are food grade materials and have selected dissolving properties, such that it remains in substantially solid form before use, and dissolves due to human body temperatures and moisture during use to release the agent material in a desired timed release and dosage.

U.S. Pat. No. 5,859,048 relates to pharmaceutics for rectal administration in which at least either a pharmacologically active ingredient or a mucousal absorption enhancer is caused to form a complex with a high molecular compound which is soluble in water at pH 5 or higher. The ingredient and the enhancer are uniformly dispersed in a fatty suppository base.

U.S. Pat. No. 5,436,009 relates to a sustained release suppository comprising in a usual *suppository base, such as a fat having a melting range of from 29° C. to 38° C., i) a water-soluble therapeutically active substance, ii) a physiologically acceptable organic substance that is swellable in contact with water, such as hydroxypropylmethylcellulose, and iii) a hydrophobic silicium dioxide.

U.S. Pat. No. 4,853,211 relates to an effervescent vaginal suppository composition containing a stabilizer, such as anhydrous sodium sulfate, anhydrous silica gel, dried magnesium silicate, dried aluminum silicate, dried calcium carboxymethylcellulose, dried microcrystalline cellulose, dried starch and dried calcium phosphate, or mixtures thereof, preferably in an amount of from 0.1 to 20% based on the weight of said effervescent vaginal suppository composition.

U.S. Pat. No. 4,698,359 relates to a medicated suppository for use in the vaginal or rectal cavity comprising a medicament, a mixture of triglycerides of fatty acids, a gel forming agent and a gel dispersing agent.

U.S. Pat. No. 4,402,692 relates to a medicament capsule encapsulating an effective ingredient. The medicament capsule is formed of a hard capsule shell made of a mixed ester of a cellulose ether, e.g. alkyl-, hydroxyalkyl- and hydroxyalkyl alkylcelluloses, esterified with aliphatic monacyl groups and acidic succinyl groups. When the capsule is inserted into the rectum, the capsule shell is disintegrated and the rectally absorbable effective ingredient is released into the rectum.

SUMMARY OF THE INVENTION

The present invention in one preferred aspect relates to a suppository for administration of at least one bioactive substance, said suppository comprising i) a polymer composition comprising at least one biocompatible polymer, wherein the biocompatible polymer is essentially non-biodegradable; and ii) a controlled release formulation for controlled release of said at least one bioactive substance, said formulation comprises at least one first polymer and/or at least one second polymer, wherein the melting point of said at least one first polymer is lower than the melting point of said at least one second polymer; and wherein preferably, the suppository essentially does not swell when contacted with an aqueous fluid.

The polymer composition according to the present invention comprises a biocompatible polymer that essentially does not swell when being contacted by moisture. The biocompatible polymer is also essentially non-biodegradable and is thus essentially not degraded during use when forming part of e.g. a suppository used in therapeutical methods including surgery.

At least part of the polymer composition comprising the biocompatible polymer preferably further comprises a plurality of interlinked, open cells that are accessible to mucousal membrane fluids and capable of containing such aqueous fluids. The contacting of the polymer composition with an aqueous fluid such as moisture secreted from the mucousal membrane under practical circumstances preferably results in essentially no fluid entering the open, accessible cells. The term "essentially no fluid" will be understood to mean an amount of fluid that results in no dehydration, or at least essentially no dehydration of the mucousal membrane in contact with the suppository according to the invention, while still allowing the fluid to contact a medicament comprised in open, accessible cells, optionally in encapsulated form, wherein the contacting of the fluid and the medicament, or the encapsulation thereof, results in the delivery of the medicament to the mucousal membrane in a pharmaceutically active amount. Dehydration of a mucousal membrane is evident from clear signs of irritatation of the mucousal membrane tissue. Irritation is routinely diagnosed by a medical practitioner, or by the individual sensing an itching or developing a rash in a body cavity region.

The invention thus in one embodiment pertains to a suppository comprising a polymer composition having a permeability for aqueous fluids, including body fluids, that results—under practical circumstances—in entry of such body fluids into a plurality of open cells comprised in the polymer composition essentially without dehydration of mucousal membrane tissue contacting the suppository.

Any biocompatible polymer that is essentially not degraded during use and essentially does not swell when being contacted by moisture can be used in accordance with the present invention. The terms "not degraded" and "does not swell" shall in the following be used within the meaning "essentially not degraded" and "essentially does not swell", respectively, as defined herein below.

The non-biodegradable polymer provides the polymer composition with a desirable degree of flexibility and ensures that a firm contact is established between the surface of the suppository and e.g. a mucousal membrane in a body cavity of an individual wherein the suppository is positioned. Preferably, the controlled release formulation has a softening point, so that the suppository is essentially rigid at room temperature, whereas the suppository is essentially soft or less rigid at body temperature. This can be measured by e.g. measuring the rigidity of the suppository by any state of the art method.

The suppository preferably comprises a bioactive substance including a medicament capable of being controllably released in the body cavity in question. As the suppository is not degraded during use it will provide a prolonged release of a medicament in the local environment. With which the suppository is in operable contact.

The suppositories according to the present invention in one embodiment solves the problem of how to provide medicaments to a local environment without generating—at essentially the same time—a systemic effect caused by caused by solvation, melting or otherwise, of the vehicle acing as a carrier of the medicament. This technical effect is in sharp contrast to state of the art suppositories made of fat-like substances that are degraded during use, typically through a process of melting or dissolving the carrier matrix.

The degradation of suppositories has the effect that administration of the medicament is not targeted to a local environment over a prolonged period of time. As a local environment is not targeted exclusively with state of the art suppositories, the medicament is taken up by the organism and exerts a systemic effect in the entire body.

The present invention in one preferred embodiment is aimed at ensuring a direct delivery of a medicament to a local environment while essentially preventing the medicament from being taken up by the body and thereby exerting a systemic effect. Furthermore, the biocompatible polymer does not melt or disintegrate, so that the medicament preferably is essentially retaining in a local environment. The present invention thus provides a means for sustained release administration of a medicament to a predetermined, local environment without essentially generating any systemic effects. However, in other embodiments of the present invention a systemic effect may be desirable.

Hence, the advantages of suppositories according to the present invention are:
i) physiological compliance
ii) fast adjustment to the shape of any body cavity
iii) large contact surface between suppository and mucosal membrane
iv) increased transport and mobility of the bioactive substance
v) water solubility of the bioactive substance
vi) local administration of the bioactive substance
vii) promotes wound healing

DEFINITIONS AND TECHNICAL TERMS

Biocompatible Material

Figure 1A:
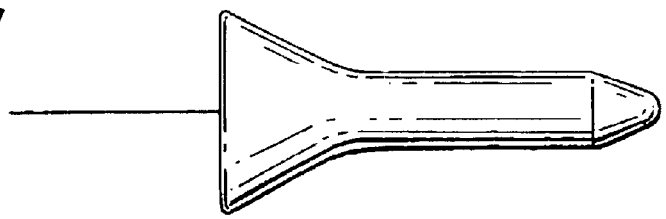
FIG. 1. Example of suitable shape of a rectal suppository.

Material suitable for contacting body tissue including mucousal membranes. Biocompaticle materials do not induce an acute or chronic inflammatory response when interacting with biological material.

Biocompatible Polymer

Biocompatible material in the form of a polymer. In one preferred embodiment the biocompatible polymer is polyurethane. Polyurethane is manufactured by reacting at least one isocyanate with at least one polyol. Preferably the isocyanate is a diisocyanate. Polyurethane made from long chain diols will produce linear polymers, which are very soft. Polyurethane made from triols or higher rate polyols will be crossbound and thereby stronger and harder.

Polyols of desirable molecular weights and chain lengths are selected so that their average functionality defined by the ratio of the amount of diol to the amount of triol and/or higher functionalities are suitable for the present invention. Such polyols may be further characterised by the skilled person according to the strength, hardness, Shore A hardness, recovery creep, flexible modulus, storage modulus, loss modulus, and compression modulus of the manufactured polymer composition.

Methods of manufacture may be selected from any state of the art method, including any suitable one-shot technique (polyisocyanat, HMW polyol and chain extending agent mixed and reacted), and any prepolymerisation technique (prepolymer between polyisocyanat and HMW polyol, thereafter reaction with chain extending agent).

When the biocompatible polymer according to the invention is a polyurethane, the reactants are used in relative amounts such that the NCO/OH ration is preferably within the overall range of about 0.7 to 1.3. The reactants can be mixed at room temperature or at the minimum elevated temperature most convenient considering the need to pour and agitate the reactants. The mixture of organic compounds containing active hydrogen containing groups can be premixed or added individually or all brought together at the same time. The organic compounds containing active hydrogen containing groups can be added to the polyisocyanate, or the polyisocyanate can be added to the organic compounds. The reaction is exothermic and cooling is sometimes applied to slow the reaction and to keep it within reasonable temperature limits. The process is effected simply by mixing the reactants.

Any suitable organic polyisocyanate may be used in the invention including aromatic, aliphatic and heretocyclic polyisocyanates. In other words, two or more isocyanate radicals may be bonded to any suitable divalent or higher polyvalent organic radical to produce the organic polylsocyanates which are useful in the present invention including acyclic, alicydic, aromatic and heterocyclic radicals Polyisocyanates with condensed rings such as the uretdion ring, as exemplified by 1,3-bis(4-methyl-3-isocyanato-phenyl) uretdion and the like are operable. Generally diisocyanates are used. However, triisocyanates and isocyanates of even higher functionality also can be used subject to the limitation that the sum of all the reactive groups on the tri- and higher functionality isocyanates as well as on the other reactive compounds present is preferably not greater than about 20 mol percent of all the reactive groups, other than NCO, that are present.

Suitable representative organic polyisocyanates are ethylene diisocyanate, ethylidene diisocyanate, propylene-1,2-diisocyanate, cyclohexylene-1,2-diisocyanate, m-phenylene-diisocyanate, 2,4-tolouene diisocyanate, 2,6 tolouene diisocyanate, 3,3'-dimethyl-4,4'biphenylele diisocyanate, 3,3'-dimethoxy-4,4'-biphelynene diisocyanate, 3,3'-diphenyl-4,4'biphenylene diisocyanate, 4,4'-biphenylene diisocyanate, 3,3'-dicholoro-4,4'-biphenylene diisocyanate, 1,5-naphtalene diisocyanate, furfurylidene diisocyanate, or polyioscyanates in a blocked or inactive form such as the bisphenyl carbamates of 2,4 or 2,6-tolouene diisocyanate, p,p'-diphenylmethane diisocyanate, and the like.

Any suitable organic compound, other than polyesters, containing at least two active hydrogen containing groups as determined by the Zerewitinoff method, said groups being reactive with an isocyanate group, may be in the mixture thereof that is reacted with an organic polyisocyanate in accordance with the process of the invention. The active hydrogen atoms are usually attached to oxygen, nitrogen or sulphur atoms. Thus, suitable active hydrogen containing groups as determined by the Zerewitinoff method which are reactive with an isocyanate group include —OH, —NH₂, —NH—, —COOH, —SH and the like. Examples of suitable types of organic compounds containing at least two active hydrogen containing groups, which are reactive with an isocyanate group are polyhydric polyalkylene ethers, polyhydric polythioethers, polyacetals, aliphatic polyols, including alkane, alkene and alkyne diols, triols, tetrols and the like, aliphatic thiols having two or more —SH groups; polyamines including aromatic, aliphatic and heterocyclic diamines, triamines, trtramines and the like; polyaralkylene ethers such as propylene oxide and ethylene oxide adducts of resorcinol, hydroquinone, bisphenol A and the like; as well as mixtures thereof. Of course, compounds which contain two or more different groups within the above-defined classes may also be used in accordance with the process of the present invention such as for example amino alcohols which contain an amino group and a hydroxyl group, amino alcohols which contain two amino groups and one hydroxyl group and the like. Also, compounds may be used which contain one —SH group and one —OH group or two —OH groups and one —SH group as well as those which contain an amino group and an —SH group and the like.

Any suitable polyhydric polyalkylene ether as well as mixtures thereof may be used such as, for example, the condensation product of an alkylene oxide or of an alkylene oxide with a polyhydric alcohol. Any suitable polyhydric alcohol may be used in producing those ethers such as, for example, ethylene glycol, 1,3-propylene glycol, 1,2-propylene glycol, 1,4 butylene glycol, 1,3-butylene glycol, 1,2-butylene glycol, 1,5-pentane diol, 1,4pentane diol, 1,3-pentane diol, 1,6-hexane diol, 1,7-heptane diol, glycerine, trimethylol propane, 1,3,6-hexanetriol, triethanol amine, pentaerythritol, sorbitol and the like. Any suitable alkylene oxide may be used such as, for example, ethylene oxide, propylene oxide, butylene oxide, amyfene oxide and the like. Of course, the polyhydric polyalkylene ethers can be prepared from other starting materials such as, for example, tetrahydrofuran, epihalohydrins, and the like as well as aralkylene oxides such as, for example, styrene oxide and the like. The polyhydric polyalkylene ethers may have wither primary or secondary hydroxyl groups and preferably are polyhydric polyalkylene ethers prepared from alkylene oxides having from two to five carbon atoms such as, for example, polyethylene ether glycols, polypropylene ether glycols, polybutylene ether glycols and the like. Trihydric or higher polyhydric alcohol such as glycerine, trimethylol propane, pentaerythritol and the like may also be used in the preparation of the polyhydric polyalkylen ethers so that some branching exists in the product.

Any suitable polyhydric polythioether may be used such as, for example, the condensation product of thiodiglycol of the reaction product of a polyhydric alcohol such as is disclosed above for preparation of the hydroxyl polyethers with any other suitable thioether glycol. Other suitable polyhydric polythioethers are disclosed in U.S. Pat. Nos. 2,862,972 and 2,900,368.

Any suitable aliphatic polyol may be used including alkane diols such as, for example, ethylene glycol, 1,3-propylene glycol, 1,2-propylene glycol, 1,4-butylene glycol, 1,3butylene glycol, 1,5-pentane diol, 1,4-pentane diol. 1,3-pentane diol, 1,6-hexane diol, 1,7-heptane diol, 2,2-dimethyl 1-1,3-propane diol, 1,8-octane diol and the like including 1,20-eicosane diol and the like; alkene diols such as, for example, 1-butne-1,4-diol, 1,3-butadiene-1,4-1,4-diol, 2-pentene-1,5-diol, 2-hexene-1,6-diol, 2-heptene-1,7-diol and the like; alkyne diols such as, for example, 2-butyne-1,4-diol, 1,5-hexadiene-1,6-diol and the like, alkane triols such as, for example, 1,3,6-hexanetriol, 1,3,7-heptane triol, 1,4,8-octane trial, 1,6,12-dodecane triol and the like; alkene triols such as, 1-hexene-1,3,6-triol and the like; alkyne triols such as, 2-hexyne-1,3,6-triol and the like; alkane tetrols such as, for example, 1,2,5,6-hexane tetrol and the like; alkene tetrols such as, for example, 3-heptene-1,2,6,7-tetrol and the like; alkyne tetrols such as for example 4octyne-1,2,7,8-tetrol and the like.

Any suitable polyacetal may be used, such as, for example, the reaction product of formaldehyde or other suitable aldehyde with a polyol such as hose disclosed above Any suitable polycarboxylic acid may be used such as, for example, oxalic acid, malonic acid, succinic acid, glutaric acid, adipic acid, pimelic acid, suberic acid, axelaic acid, sebacic acid, brassylic acid, thapsic acid, maleic acid, fumaric acid, glutaconic acid, alpha-hydromuconic add, beta-hydromuconic acid, alpha-butyl-alpha-ethyl-glutaric acid, alpha,beta-diethylsuccinic acid, isophthalci acid, terephthalic acid, hemimellitic acid, trimellitic acid, trimesic acid, mellophanic acid, prehnitic acid, pyromellitic acid, benzenepentacarboxylic acid, 1,4-cyclohexanedicarboxylic acid, 3,4,9,10-perylene-tetracarboxylic acid and the like.

Any suitable aliphatic thiol including alkane thiols containing two or more —SH groups such as, for example, 1,2-ehtane dithiol, 1,2-propane dithiol, 1,3-propane dithiol, 1,6-hexane dithiol, 1,3,6-hexane trithiol and the like; alkene thiols such as, for example, 2-butene-1,4-dithiol and the like; alkyne thiols such as, for example, 3-hexyne-1,6-dithiol and the like may be used.

Any suitable polyamine may be used including, for example, aromatic polyamines such as, for example, p-amino aniline, 1,5-diamino naphthalene, 2,4diamino tulouene, 1,3,5benzene triamine, 1,2,3-benzene triamine, 1,4,5,8-naphthalene tetramine and the like; aliphatic polyamines such as for example ethylene diamine, 1,3-propylene diamine, 1,4-butylene diamine, 1,3-butylene diamine, diethylene triamine, triethylene tetramine, 1,3,6-hexane triamine, 1,3,5,7-heptane tetramine and the like; heterocyclic polyamines such as, for example, 2,6-diamino pyridine, 2,4-diamino 5-aminomethylpyrimidine, 2,5-diamino-1,3,4-thiadiazol and the like.

Other alcohol compounds which do not necessarily fit within any of the previously set forth classes of compounds and which nevertheless contain active hydrogen containing groups which are quite suitable for the production of the polyurethane plastics of the present invention are pentaerythritol, castor oil, sorbitol, triethalolamine, mannitol, N,N,N',N'-tetrakis (2-hydroxy propyl) ethylene diamine, as well as compounds of any of the classes set forth above which are substituted with halogen such as, for example chloro, iodo, bromo, and the like; nitro; alkoxy, such as for example methoxy, ethoxy, propoxy, butpoxy and the like; carboalkoxy such as for example carbomethoxy, carbethoxy and the like; dialkyl amino such as for example dimethyl amino, diethyl amino, dipropyl amino, methylethyl amino and the like; mercapto, carbonyl, thriocarbonyl, phosphoryl, phosphate and the like.

A catalyst may be used in the reaction mixture leading to the production of the cross-linked thermoplastic polyurethanes. Suitable catalysts are, for example, tertiary amines, such as, for example, triethylene diamine, N-methyl morpholine, N-ethyle-morpholine, diethyl ethanolamine, N-coco morpholine, 1-methyl-4-dimethylamino ethyl piperazine, 3-methoxy-N-dimethyl propyl amine, N-dimethyl-N'methyl isopropyl propylene diamine, N,N-diethyl-3-diethyl amino propyl mine, dimethyl benzyl amine and the like. Other suitable catalysts are for example, tin compounds such as, stannous chloride, tin salts of carboxylic acids such as dibutyl tin di-2ethyl hexoate, stannous octoate, tin alcoholates such as dibutyl tin dibutoxide as well as other organo metallic compounds. If desired for any purpose a conventional reaction regulator such as water, a triol, urea, substituted urea, amines or the like can also be used in the normal manner.

Suitable compounds for manufacturing thermoplastic polyurethanes are disclosed in U.S. Pat. No. 3,356,650 and in U.S. Pat. No. 4,769,435, which are incorporated by reference.

Further polymer materials suitable in accordance with the present invention are preferably those which are possible to process by extrusion, solution or in the form of a dispersion. Most preferred are those which are available in a food grade or pharmaceutical grade quality. Examples of such polymers are cellulose acetate, polyamide, polyethylene, polyethylene terephthalate, polypropylene, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA). styrene-butadiene-styrene (SBS) and styrene-isoprene-styrene (SIS).

Apart from the above-mentioned biocompatible polymers that are non-biodegradable, the present invention also pertains to biocompatible polymers in a form which erodes at a substantially slower rate than the rest of the matrix. The biocompatible polymer may thus be formed so that it comprises a matrix of one or more substantially water soluble crystalline polymers and a surface active agent, wherein such a biocompatible polymer is eroded in the aqueous phase at a substantially slower rate than that of the matrix material. Comprising the medicament. This difference in erosion results initially in a substantially constant erosion of the area of the composition for controlled release comprising the matrix comprising the medicament, and only subsequently is the biocompatible, polymer substantially eroded.

Body Cavity

An opening and/or orifice of the body. For example a body cavity may be the rectal, vaginal, urethral, otogenic or nasal orifice of the body.

Body Temperature

A normal temperature in a cavity into which a suppository is to be inserted. Typical values range from about 35° C. to about 42° C.

Central Core

The suppository may comprise a central part having at least one physical or chemical parameter differing from that of a surrounding part. This physical parameter could for example be bond strength between restorative materials, brinell hardness number, coefficient of friction, coefficient of thermal expansion, surface tension, density, flexible modulus, elastic modulus, impact strength, Knoop hardness number, melting temperature, glass-rubber transition temperature, Mohs' hardness, penetration coefficient, shear strength, shore A hardness, shore D hardness, strain in compression, tear strength, transverse strength, ultimate compressive strength, ultimate tensile strength. Vickers hardness, yield strength. The parts could also differ chemically from one another. The chemical difference could be reflected in a difference in the at least one physical parameter.

According to one embodiment, the suppository is hollow. Preferably the cavity inside the suppository extends axially from one end of the suppository. The cavity is adapted to receive an insertion means. The insertion means may be a stick adapted to press the suppository into position in the body cavity and to provide the suppository with sufficient strength during the insertion.

Similarly, the suppository may comprise a coating on at least part of the surface of the suppository, said coating differing from the central core and/or the surrounding part in respect of at least one chemical or physical parameter.

Coating

A coating is a layer provided on at least part of the surface of the suppository according to the invention. The coating differs from other parts of the suppository in respect of at least one physical or chemical parameter.

Contact

Contact capable of mediating release of any medicament contacted by a composition or a suppository.

Controllable Release

Release of e.g. a bioactive substance such as a medicament at at least one predetermined rate over a predetermined period of time. The medicament may accordingly be released over a prolonged period of time. The rate of release may be approximately linear over the whole administration period or the rate may vary over time according to the desired administration profile. The release period can further be controlled and prolonged by encapsulating the medicament into e.g. microcapsules or any other controlled release formulation, which will release the medicament over a prolonged period into the body cavity. However, part of or essential all of the bioactive substance may also be released in a relatively short time.

Bioactive substances are also capable of being released from the controlled release formulation into adjacent tissues or fluids by diffusion and polymer degradation mechanisms. Manipulation of these mechanisms also can influence the release of the bioactive substance into the surroundings at a controlled rate. For example, the polymer matrix can be formulated to degrade after an effective and/or substantial amount of the bioactive material is released from the matrix. Release of a material having a low solubility in water, as for example a peptide or protein, typically requires the degradation of a substantial part of the polymer matrix to expose the material directly to the surrounding tissue fluids. Thus, the release of the biologically active material from the matrix can be varied by, for example, the solubility of the bioactive material in water, the distribution of the bioactive material within the matrix, or the size, shape, porosity, solubility and biodegradability of the controlled release formulation, including a polymer matrix comprising at least one polyethylene glycol. The release of the biologically active material from the matrix is controlled relative to its intrinsic rate by varying e.g. the polymer molecular weight, by introducing polyethylene glycols of differing chain length and consequently differing melting temperatures into the controlled release formulation, or by adding a rate modifying agent to provide a desired duration and rate of release.

Additives can be used to advantage in further controlling the desired release rate of a bioactive substance for a particular treatment protocol. For example, if the resulting polymer composition or controlled release formulation is too impervious to water, a pore-forming agent can be added to generate additional pores. Any biocompatible water-soluble material can be used as the pore-forming agent. The amount of pore-forming agent (and size of dispersed particles of such pore-forming agent, if appropriate) within the polymer composition will directly affect the size and number of the pores in the polymer system.

Pore-forming agents include any pharmaceutically acceptable organic or inorganic substance that is substantially miscible in water and body fluids. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of pore-forming agent incorporated into the polymer system.

In addition, the polymer composition of the invention can also comprise polymer blends of the polymer of the invention with other biocompatible polymers. Blends of the polymer of the invention with such other polymers may offer even greater flexibility in designing the precise release profile desired for targeted drug delivery.

Controlled Release Formulation

Formulation comprising at least one bioactive substance, for example a medicament, which is capable of controllable release of said bioactive substance.

Essentially does not Swell

The suppository when brought into contact with moisture or water does not swell to any extent, which negatively affects its function. It furthermore implies that the size of the suppository does not essentially change after insertion into the body cavity. The shape of the suppository can change after insertion into a body cavity in the absence of any swelling. A change of size due to swelling would be disadvantageous to the sensitive mucousal membranes of the body cavity, and swelling could also cause troubles when the suppository is changed.

Essentially Non-biodegradable

The polymer should not disintegrate when contacted with a body tissue, such as a mucousal membrane within the time limits of use as defined by the invention. Also, the polymer should essentially not dissolve when in contact with moisture or a body tissue. In this context essentially means that the polymer should not disintegrate to any extent such as loss of strength or loss of weight, which would negatively affect its geometric properties and strength.

First Polymer

A first polymer according to the present invention is a polymer, which constitutes part of a controlled release formulation and which in any given embodiment of the present invention has a lower melting temperature than the second polymer of said embodiment Glass Transition Temperature Temperature of a given material determined e.g. by means of stress/strain measurement, at which the modulus of the material changes from i) a relatively high value obtained in a low temperature, "glassy" state of the material to ii) a lower value obtained in the transition region to the higher temperature "rubbery" state of the material, as described e.g. in U.S. Pat. No. 4,594,380. The glass-rubber transition temperature depends e.g. on the chemical nature of the polymer in question, such as the degree of cross-linking of a cross-linked polymer. Where the polymer is polyurethane, starting compounds such as a specified diol and/or triol in combination with a diisocyanate will determine the glass-rubber transition temperature by determining e.g. the cross-linked nature of polyurethane which can be produced from these starting compounds. The cross-linking will depend on the proportion of the diol to the triol that is used in the polymerisation process. In general, the greater the proportion of triol the greater will be the glass-rubber transition temperature. Where the polyurethane precursors comprise, for example, a diisocyanate and an oxyalkylated triol, the glass-rubber transition temperature of the cross-linked polyurethane which can be produced from the precursors will depend on the molecular weight of the oxyalkylated trial. In general, the lower the molecular weight of the triol the greater will be the glass-rubber transition temperature. The man skilled in the art will readily be able to select suitable combinations of polyurethane precursors.

Local Environment

A local environment is preferably an environment confined to the body cavity wherein the suppository is positioned, and any neighbouring tissue into which the medicament is administered.

Medicament

The terms "drug," "medicament," or "bioactive substance" (i.e., biologically active substance) as used herein include, biologically, physiologically, or pharmacologically active substances that act locally or systemically in the human or animal body. The "drug," "medicament," or "bioactive substance" can be present in any suppository for use either prophylactically, therapeutically, in connection with treatment of an individual, such as a human or any other animal, As an alternative, the present invention also pertains to the release of diagnostic agents and/or cosmetic agent.

Various forms of the medicaments or biologically active materials can be used which are capable of being released from the controlled release formulation, including a polymer matrix, including a matrix comprising at least one polyethylene glycol, including a matrix comprising comprising at least one first polymer, preferably a polyethylene glycol, and at least one second polymer, preferably a polyethylene glycol, wherein the melting point of said at least one first polymer is lower than the melting point of said at least one second polymer into adjacent tissues or fluids.

The medicaments are at least very slightly water-soluble, preferably moderately water-soluble, and are diffusible through the polymer composition. They can be acidic, basic, or salts. They can be neutral molecules, polar molecules, or molecular complexes capable of hydrogen bonding. They can be in the form of ethers, esters, amides and the like, which are biologically activated when administered to the human or animal body.

The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The bioactive substance of the invention can vary widely with the purpose for the suppository. The active substance(s) may be described as a single entity or a combination of entities. The controlled release formulation is designed to be used with biologically active substances having high-water-solubility as well as with those having low water-solubility to produce a delivery system that has controlled release rates.

Non-limiting examples of useful biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythrpoietic agents, expectorants, gastrointestinal sedatives hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants vitamins, antigenic materials, analgetics and prodrugs.

Specific examples of useful biologically active substances from the above categories include (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, zyrilamine maleate, doxylamine succinate, and phenyltcloxamine citrate; (d) decongestants such as phenylephrine hydrochloride, chenylpropanolamine hydrochloride, pseudoephedrine hydrochloride, and ephedrine; (e) various alkaloids such as codeine phosphate, codeine sulfate and morphine—(f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, particularly those useful in vaccine applications.

Analgetics are pharmaceuticals that may be used to alleviate pain. In general analgetics may belong to one of 3 groups, i) opiod analgetics, ii) weak non-opiod analgetics and iii) psychopharmacological drugs, lidocain analogues and antiepileptica used to alleviate pain. In a preferred embodiment of the present invention the analgetic is lidocain.

To further illustrate, antimetabolites which can be formulated in the subject polymers include, but are not limited to, methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. Vinca alkaloids and epipodophyllotoxins may include, but are not limited to vincristine, vinblastine, vindesine, etoposide, and teniposide.

Nitrosoureas can also be provided in the subject matrizes, including carmustine, lomustine, semustine and streptozocin.

Hormonal therapeutics can also be included in the polymeric matrices, such as corticosteriods (cortisone acetate, hydrocortisone, prednisone, prednisolone, methyl prednisolone and dexamethasone), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole).

Other compounds which can be disposed in the controlled release formulation of the present invention include those classified as e.g. investigational drugs, and can include, but are not limited to alkylating agents such as Nimustine AZQ, BZQ, cyclodisone, DADAG, CB10-227, CY233, DABIS maleate, EDMN, Fotemustine, Hepsulfarn, Hexamethylmelamine, Mafosamide, MDMS, PCNU, Spiromustine, TA-077, TCNU and Temozolomide; antimetabolites, such as acividin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, SWA773U$_7$ BWA502U, Amonafide, m-AMSA, CI-921, Datelliptum, Mitonafide, Piroxantrone, Aclarubicin, Cytorhodin, Epirubicin, esorubicin, Idarubicin, Iodo-doxorubicin, Marcellomycin, Menaril, Morpholino anthracyclines, Pirarubicin, and SM-887; microtubule spindle inhibitors, such as Amphethinile, Navelbine, and Taxol; the alkyl-lysophospholipids, such as BM41-440, ET-18-OCH3, and Hexacyclophosphocholine; metallic compounds, such as Gallium Nitrate, CL286558, CL287110. Cycloplatam, DWA2114R, NK121, Iproplatin, Oxaliplafin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721; and Toremifene, Trilosane, and zindoxifene.

Antitumor drugs that are radiation enhancers can also be formulated in the subject controlled release formulation. Examples of such drugs include, for example, the chemotherapeutic agents 5'-fluorouracil, mitomycin, cisplatin and its derivatives, taxol, bleomycins, daunomycins, and methamycins.

The invention may, additionally, be used for the treatment of infections. For such an application, antibiotics, either water soluble or water insoluble, may be immobilized/formulated in the subject polymers. Antibiotics are well known to those of skill in the art, and include, for example, penicillins, cephalosporins, tetracyclines, ampicillin, aureothidin, bacitracin, chloramphenicol, cycloserine, erythromycin, gentamicin, gramacidins, kanamycins, neomycins, streptomycins, tobramycin, and vancomycin.

The subject polymers can also be formulated with peptide, proteins or other biopolymers, e.g., such as interferons, interleukins, tumor necrosis factor, and other protein biological response modifiers.

In one embodiment, the biologically active substance is selected from the group consisting of polysaccharides, growth factors, hormones, anti-angiogenesis factors, interferons or cytokines, and pro-drugs. In a particularly preferred embodiment, the biologically active substance is a therapeutic drug or pro-drug, -most preferably a drug selected from the group consisting of chemotherapeutic agents and other anti-neoplastics, antibiotics, anti-virals, anti-fungals, anti-inflammatories, anticoagulants, an antigenic materials.

The biologically active substances are used in amounts that are therapeutically effective. While the effective amount of a biologically active substance will depend on the particular material being used, amounts of the biologically active substance from about 1% to about 65% are capable of being incorporated into the present delivery systems while achieving controlled release. Lesser amounts may be used to achieve efficacious levels of treatment for certain biologically active substances.

Pharmaceutically acceptable carriers may be prepared from a wide range of materials. Without being limited thereto, such materials include diluents, binders and adhesives, lubricants, disintegrants, colorants, bulking agents, flavorings, sweeteners, and miscellaneous materials such as buffers and absorbents in order to prepare a particular medicated suppository.

Further examples of medicaments according to the present invention are antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, β-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable medicaments may be selected from contraceptives and vitamins as well as micro- and macronutrients.

Further therapeutic agents which may be administered in accordance with the present invention include, without limitation: antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Further specific examples of bioactive substances that can be formulated in the subject polymers in accordance with the present invention include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, <a>6X chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyidopa, methylergonovine, methylphenidate, methylprednisolone, methysergide, metoclopramide, matolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystafin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyrodoxine, pyrilamine, pyrvinium, quinestrol, quinethazone, uinidine, quinine, ranitidine, rauwolfia alkaloids, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B12, vitamin C, vitamin D, vitamin E, vitamin K, xanthine, and the like.

The controlled release formulation is also suitable for the delivery of polypeptides, for example hormones such as growth hormones, enzymes such as lipases, proteases, carbohydrases, amylases, lactoferrin, lactoperoxidases, lysozymes, nanoparticles, etc., and antibodies. The controlled release formulation may also be employed for the delivery of microorganisms, either living, attenuated or dead, for example bacteria, e.g. gastrointestinal bacteria such as streptococci, e.g. *S. faecium,* Bacillus spp. such as *B. subtilis* and *B. licheniformis,* lactobacteria, Aspereillus spp., bifidogenic factors, or viruses such as indigenous vira, enterovira, bacteriophages, e.g. as vaccines, and fungi such as baker's yeast, *Saccharomyces cerevisiae* and fungi imperfect.

The controlled release formulation may also be used for the delivery of active agents in specialized carriers such as liposomes, cyclodextrines, nanoparticles, micelles and fats.

Preferred medicaments for rectal administration include hormones, antibiotics, anaesthetics, analgesics, anti-fungal compounds, bactercides, bacteriostats, anti-protozoan compounds, and anti-viral compounds.

Further examples of medicaments capable of being released from a controlled release formulation within a suppository according to the invention and into a body cavity include, but are not limited to, antihistamines (e.g., dimenhydrinate, diphenhydramine (50–100 mg), chlorpheniramine and dexchlorpheniramine maleate), analgesics (e.g., aspirin, codeine, morphine (15–300 mg), dihydromorphone, oxycodone, etc.), anti-inflammatory agents (e.g., naproxyn, diclofenac, indomethacin, ibuprofen, acetaminophen, aspirin, sulindac), gastro-intestinals, and anti-emetics (e.g., metoclopramide (25–100 mg)), anti-epileptics (e.g., phenytoin, meprobamate and nitrazepam), vasodilators (e.g., nifedipine, papaverine, dilfazem and nicardipine), anti-tussive agents and expectorants (e.g., codeine phosphate), antiasthmatics (e.g. theophylline), anti-spasmodics (e.g. atropine, scopolamine), hormones (e.g., insulin, heparin), diuretics (e.g., ethacrynic acid, bendroflumethiazide), anti-hypotensives (e.g., propranolol, clonidine), bronchodilators (e.g., albuterol), ant-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including apetite suppressants such as phenylpropanolamine). The above list is not meant to be exclusive.

Other types of medicaments include flurazopam, nimetazepam, nitrazepam, perlapine, estazolam, haloxazolam, sodium valproate, sodium cromoglycate, primidone, alclofenac, perisoxal citrate, clidanac, indomethacin, sulpyrine, flufenamic acid, ketoprofen, sulindac, metiazinic acid, tolmefin sodium, fentiazac, naproxen, fenbufen, protizinic acid, pranoprofen, flurbiprofen, diclofenac sodium, mefenamic add, ibuprofen, aspirin, dextran sulfate, carindacillin sodium, and the like.

The medicament may be in the form of a physiologically active polypeptide, which is selected from the group consisting of insulin, somatostatin, somatostatin derivatives, growth hormone, prolactin, adrenocorticotrophic hormone, melanocyte stimulating hormone, thyrotropin releasing hormone, its salts or its derivatives, thyroid stimulating hormone, luteinizing hormone, follicle stimulating hormone, vasopressin, vasopressin derivatives, oxytocin, carcitonin, parathyroid hormone, glucagon, gastrin, secretin, pancreozymin, cholecystokinin, angiotensin, human placental lactogen, human chorionic gonadotropin, enkephalin, enkephalin derivatives, endorphin, interferon (in one or more of the forms alpha, beta, and gamma), urokinase, kallikrein, thymopoletin, thymosin, motilin, dynorphin, bombesin, neurotensin, caerulein, bradykinin, substance P, kyotorophin, nerve growth factor, polymyxin B, colistin, gramicidin, bacitracin, bleomycin and neocarzinostatin. Furthermore, the medicament may be a polysaccharide, such as heparin, an antitumor agent such as lentinan zymosan and PS-K (krestin), an aminoglycoside such as e.g. gentamycin, streptomycin, kanamycin, dibekacin, paromomycin, kanendomycin, lipidomycin, tobramycin, amikacin, fradiomycin and sisomicin, a beta-lactam antibiotic, such as e.g. a penicillin, such as e.g. sulbenicillin, mecillinam, carbenicillin, piperacillin and tcarcillin, thienamycin, and cophalosporins such as cefotiam, cefsulodine, cefmenoxime, cefmetazole, cefazolin, cefotaxime, cefoperazone, ceftizoxime and moxalactam, or a nucleic acid drug such as e.g. citicoline and similar antitumor agents, for example cytarabine and 5-FU (5-fluorouracil).

Certain monomeric subunits of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

For the purposes of this application, unless expressly noted to the contrary, a named amino acid shall be construed to include both the D or L stereoisomers, preferably the L stereoisomer.

If, for instance, a particular enaritiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art and subsequent recovery of the pure enantiomers.

Medicament suitable for vaginal administration are contraceptives, hormones, antibiotics, anaesthetics, analgesics, contraction-preventers, anti-mycotica, bactericides, bacteriostats, anti-protozoan compounds, antiviral compounds, and compositions for uterus contraction. Other suitable medicaments in this respect is dermatological medicaments such as antimycotica, antipruritic compositions, and dermoprotective compositions. Another of the uses for which the controlled release formulations according to the invention is well-suited is the delivery of antimicrobial agents to the vagina. Examples of such agents are antifungals, for example imidazole antifungals such as clotrimazole, econazol, ketoconazole and miconazole, polyene antifungal antibiotics such as nystatin, and antiprotozoais such as metronidazole and omidazole.

Medicaments for administration in the ear (otogenic administration) are e.g. antibiotics, corticosteroids, local anaesthetics, and analgesics.

Medicaments for nasal administration are e.g. haemostatica, anti-allergenic compounds, antihistamines, anticholinergica, adrenergic (detumescent) compounds, and local analgesics.

The medicaments can in principle have either local effects, or systemic effects. In a preferred embodiment the suppository comprises at least one medicament that has a local effect and essentially does not have any systemic effects.

Microcapsules

The bioactive substance including a medicament according to the invention may be encapsulated in e.g. a microcapsule. The microcapsule for may be made from any suitable material. It may be a hydrophilic or a hydrophobic material. Likewise the microcapsule may be provided with a coating. This coating may be of a kind that prevents agglomeration or sticking of the microcapsules or prevents evaporation of the drug and/or a solvent comprising the drug inside the microcapsule. The invention also foresees the use of coatings providing the microcapsule with an affinity for specific cells or tissues. Such an affinity-coating may be in the form of specific amino-acid sequences or even antibodies or parts of antibodies having an affinity for specific proteins. Thereby the drug-delivery can be targeted to exactly those cells (e.g. cancer cells, metastases) to which the drug should be administered. Likewise this makes it possible to use the microcapsules for diagnostic use and the drug could in such cases be substituted by a compound suitable for labelling the targeted cells.

Agents for encapsulation include but are not limited to colloids, hydrocolloids such as gelatine, exudates such as gum arabic, tragacanth, gum karya, gum ghatti; extracts from seaweed such as agar, alginate, carrageenan and furcellaran; extracts from plants such as pectin and arabinogalactan; extracts from marine and terrestrial animals such as gelatines and other proteinaceous hydrocolloids; flours from seeds such as guar, locust bean, soya bear, proteins from seeds such as soya bean proteins; flours from cereals such as starches and microcrystalline cellulose; biosynthetic or fermentation derived hydrocolloids such as dextran, xanthan and curdlan; chemically modified hydrocolloids such as cellulose derivatives, including methyl cellulose and other derivatves, including modified starches and low methoxyl pectin; synthetic hydrocolloids such as polyvinylpyrrolidone, carboxyvinyl polymers etc.

According to one embodiment of the invention, the microcapsules contain a hydrophobic/aerophilic solid material having a maximum average particle size not exceeding 10 μm (micrometer) and which can be dispersed in water in the form of discrete microparticles, wherein the amount of solid active material in the microencapsulated product is from 22 to 71% by weight.

According to another embodiment of the invention, the microcapsules may comprise a microencapsulated oil or fat product, wherein at least one oil or fat is dispersed in the matrix material as particles or drops having an average diameter of less than or equal to 2 μm (micrometer), the oil or fat containing at least 10% by weight of highly unsaturated fatty acid, preferably omega-3 and omega-6 fatty acids, the level of free fatty acids being below 5.0% by weight and preferably below about 0.5% by weight, and the matrix material consisting of caseinate and optionally at least one carbohydrate. The oil or fat may be a marine oil, preferably a fish oil, containing at least 30% by weight of omega-3 fatty acids. Similarity, the oil or fat may be a vegetable oil, preferably borage oil, and preferably containing at least 20% by weight of omega-3 and/or omega-6 fatty acids. This oil or fat may be a natural, fermented and/or enzymatically reesterified or chemically modified oil or fat, preferably in an amount of from 10 to 65% by weight the matrix material comprises from 1 to 100% by weight caseinate and from 0 to 70% by weight of at least one carbohydrate selected from the group consisting of glucose syrup, maltodextrin, saccharose, maltose or lactose; from 0 to 10% by weight of at least one antioxidant selected from the group consisting of the vitamin antioxidants a-, ss-, r- and 6-tocopherols, ascorbic acid and derivatives thereof, carotenoids, and rosemary extract, and from 0 to 35% by weight of a spraying agent selected from the group consisting of corn starch, milk proteins, including casein, caseinate and whey proteins, preboiled or gelatinised starch, soy bean protein isolates, lactose, tricalcium phosphate, and calcium carbonate.

In the case of a water-soluble drug, the microcapsule may be prepared as a two-phase system with an inner aqueous phase comprising the drug and optionally drug-retaining or drug-stabilising compounds. This inner aqueous phase can then be emulsified with an oil-phase comprising a polymer to create a water/oil emulsion.

The polymer to be contained in the oil phase in carrying out the microencapsulation method is a polymer, which is scarcely soluble or insoluble in water and is biocompatible. Examples are such biodegradable polymers as aliphatic polymers (e.g. polylactic acid, polyglycolic acid, polycitric acid, polymalic acid), poly-alpha-cyanoacrylic acid esters, poly-beta-hydroxybutyric acid, polyalkylene oxalate (e.g. polytrimethylene oxalate, polytetramethylene oxalate), polyorthoesters, polyorthocarbonates and other polycarbonates (e.g. polyethylene carbonate, polyethylenepropylene carbonate), and polyamino acids (e.g. poly-.gamma.-benzyl-L-glutamic acid, poly-L-alanine, polygamma-methyl-L-glutamic acid). Other biocompatible high polymers are polystyrene, polyacrylic acid, polymethacrylic acid, acrylic acid-methacrylic acid copolymers, polyamides (nylon), polyethylene terephthalate (tetron), polyamino acids, silicone polymers, dextran stearate, ethylcellulose, acetylcellulose, nitrocellulose, polyurethanes, maleic anhydride-based copolymers, ethylene-vinyl acetate copolymers, polyvinyl acetate, polyvinyl alcohol, polyacrylamide, etc. These polymers may be homopolymers or copolymers of two or more monomers, or mixtures of the polymers. They may also be in the salt form.

For the emulsification procedure, a known method of effecting dispersion is used. Said method is, for example, the intermittent shaking method, the mixer method using a propeller-shaped stirrer, a turbine-shaped stirrer or the like, the colloid mill method, the homogeniser method or the ultrasonication method.

The thus-prepared W/O emulsion is then emulsified into a W/O/W triplicate-phase emulsion and subjected to an in water drying. Thus, said W/O emulsion is further added to a third aqueous phase to give a W/O/W emulsion and thereafter the solvent in the oil phase is removed to give microcapsules.

To the external aqueous phase, there may be added an emulsifying agent. As the emulsifying agent, there may be used any one capable of forming generally a stable O/W emulsion, for example an anionic surfactant (e.g. sodium oleate, sodium stearate, sodium lauryl sulfate), a nonionic surfactant [e.g. polyoxyethylenesorbitan fatty acid ester (Tween 80, Tween 60, products of Atlas Powder Co., U.S.A.), a polyoxyethylene castor oil derivative (HCO-60, HCO-50, products of Nikko Chemicals, Japan)), polyvinyl pyrrolidone, polyvinyl alcohol, carboxymethylcellulose, lecithin or gelatin. Such emulsifiers may be used either alone or in any combination.

Polymer Composition

The polymer compositions according to the present invention are compositions comprising at least one biocompatible polymer, wherein the biocompatible polymer is essentially non-biodegradable.

Oblong

By a oblong shape of the suppository is meant that the suppository has two axises of different length. Examples of oblong suppositories are suppositories formed into e.g. a cylindrical shape or a bullet-shape wherein one end of the suppository has a tapering shape.

Second Polymer

A second polymer according to the present invention is a polymer, which constitutes part of a controlled release formulation and which in any given embodiment of the present invention has a higher melting temperature than the first polymer of said embodiment.

Softening Point

The softening point according to the present invention, is the temperature at which a polymer or a mixture of polymers becomes soft. Thus, at this temperature, the polymer does not flow and is not in the molten state. The softening point according to the present invention is preferably the temperature at which a needle with a circular cross-section of 1 mm$^2$ with a standard load penetrates 1 mm into the sample, according to ASTM standard D1525.

Suppository

A mass comprising at least one bioactive substance, which is adapted for introduction into a body cavity. Suppositories are preferably solid at lower temperatures, such as for example room temperature and/or temperatures below room temperature. Suppositories according to the present invention are preferably soft at body temperature, but they preferably do not melt at body temperature. Furthermore suppositories according to the present invention comprises i) a polymer composition comprising at least one biocompatible polymer, wherein the biocompatible polymer is essentially non-biodegradable; and ii) a controlled release formulation for controlled release of said at least one bioactive substance, said formulation comprising at least one first polymer and/or at least one second polymer, wherein the melting point of said at least one first polymer is lower than the melting point if said at least one second polymer; and wherein the suppository essentially does not swell when contacted with an aqueous fluid.

DETAILED DESCRIPTION OF THE INVENTION

The suppository according to the present invention is especially advantageous for administration of local anaestheticum after rectal surgery and especially after haemorrhoid surgery. Under these conditions there is a need for a local and prolonged treatment of the rectum without any need for systemic treatment of the body due to uptake and distribution of the medicament throughout the body.

The suppository according to the invention may also advantageously be used as a vagitory comprising a local anaesthetic after birth accompanied e.g. by rupture or episitomy (cutting of the vagina).

However, the suppository according to the invention may also be used for nasal and otogenic administration of medicaments of e.g. anti-allergic medicaments, medicaments to improve fluid passage such as the passage of secrete, or as a means to stop bleeding.

Although the suppositories according to the present invention, preferably are suitable for local administration, the suppositories according to the present invention may in one embodiment be suitable for systemic administration of one or more bioactive substances.

According to an especially preferred embodiment of the invention the biocompatible polymer essentially does not swell upon contact with water or moisture. It is a great advantage that the size of the suppository does not change after insertion into the body cavity. It is a further advantage that the suppository has a very low affinity for water and therefore does not deprive the mucous of the body cavity of moisture, which would cause irritation to the mucus. Furthermore it is an advantage that the whole suppository can be removed after use practically not leaving any part of the polymer backbone of the suppository in the body cavity. Suppositories that are adapted to melt or dissolve within the body cavity leave an undesirable amount of polymer or melted lipid behind, which may cause irritation to the body tissue in the body cavity.

In one aspect of the present invention there is provided a suppository comprising a polymer composition comprising at least one biocompatible polymer, wherein the biocompatible polymer is essentially non-biodegradable, and wherein the suppository essentially does not swell when contacted with an aqueous fluid, such as e.g. a liquid, for example water.

In one aspect the present invention relates to such a polymer composition per se. For example the invention relates to such polymer compositions that do comprise and/or is not in contact with a controlled release formulation and/or a bioactive substance.

In one embodiment the polymer composition may comprise a biocompatible polymer which is essentially non-biodegradable and is essentially non-permeable to an aqueous fluid.

The term "essentially non-permeable to an aqueous fluid" indicates that the polymer essentially does not take up any liquid when being contacted by such liquid, e.g. under practical circumstances. It is within the meaning of the term "essentially non-permeable" that the uptake of any liquid including water is less than 1% under practical circumstances, such as less than 0.5%, for example less than 0.2%, such as less than 0.1%.

The polymer composition according to the present invention may comprise open cells, which are accessible to liquid or moisture from an environment outside the cell (see herein below). The term "essentially non-permeable to an aqueous fluid" is not meant to encompass, that an aqueous fluid can not enter open cells of a polymer composition from an environment connected to said open cell. The term "essentially non-permeable to an aqueous fluid" only indicates that an aqueous fluid may not cross the wall of the cells of a polymer composition, but can enter the cells through their opening to the outside.

The term "essentially non-biodegradable" shall be understood to mean that the polymer does not react under practical circumstances with substances that results in any substantial decomposition of the polymer. The amount of polymer measured as weight percent, i.e. dry weight of polymer per dry weight of polymer composition, is substantially unchanged at least during use of the suppository under practical circumstances, and preferably for a period of time substantially exceeding the period during which the polymer is used under practical circumstances. The term "essentially non-biodegradable" thus also refers to an unchanged dry weight of polymer per dry weight of polymer composition over a period of at least 1 week, for example 1 month, and preferably 1 year.

The polymer composition preferably has a density of from about 100 gram per liter to about 250 gram per liter, such as a density of from about 100 gram per liter to about 110 gram per liter, for example a density of from about 110 to about 120 gram per liter, such as a density of from about 120 gram per liter to about 125 gram per liter, for example a density of from about 125 to about 130 gram per liter such as a density of from about 130 gram per liter to about 135 gram per liter, for example a density of from about 135 to about 140 gram per liter such as a density of from about 140 gram per liter to about 145 gram per liter, for example a density of from about 145 to about 150 gram per liter such as a density of from about 150 gram per liter to about 155 gram per liter, for example a density of from about 155 to about 160 gram per liter such as a density of from about 160 gram per liter to about 165 gram per liter, for example a density of from about 165 to about 170 gram per liter such as a density of from about 170 gram per liter to about 175 gram per liter, for example a density of from about 175 to about 180 gram per liter such as a density of from about 180 gram per liter to about 185 gram per liter, for example a density of from about 185 to about 190 gram per liter, such as a density of from about 190 gram per liter to about 195 gram per liter, for example a density of from about 195 to about 200 gram per liter, such as a density of from about 200 gram per liter to about 210 gram per liter, for example a density of from about 210 to about 220 gram per liter, such as a density of from about 220 gram per liter to about 230 gram per liter, for example a density of from about 230 to about 240 gram per liter, such as a density of from about 240 gram per liter to about 250 gram per liter.

The compression modulus of the suppository at ambient temperature, such as e.g. 22 degree centigrade, is preferably from about 10 kPa to about 40 kPa, such as from about 10 kPa to about 12 kPa, for example from about 12 kPa to about 14 kPa, such as from about 14 kPa to about 16 kPa, for example from about 16 kPa to about 18 kPa such as from about 18 kPa to about 20 kPa, for example from about 20 kPa to about 22 kPa, such as from about 22 kPa to about 24 kPa, for example from about 24 kPa to about 26 kPa, such as from about 26 kPa to about 28 kPa, for example from about 28 kPa to about 30 kPa, such as from about 30 kPa to about 32 kPa, for example from about 32 kPa to about 34 kPa, such as from about 34 kPa to about 36 kPa, for example from about 36 kPa to about 38 kPa, such as from about 38 kPa to about 40 kPa.

The polymer composition comprises a mixture of "cells" that may be closed or open. Closed cells are discrete entities that are contained in and surrounded by a biocompatible polymer, and they are not accessable to liquid or moisture provided by an external environment such as e.g. moisture secreted from or released by mucous surfaces of a body cavity.

Open cells are present when the biocompatible polymer forms an interconnected network in the form of a matrix composition that allows for interconnections between adjacently positioned cells Hence, open cells are accessable to liquid or moisture provided by an environment outside the cell. An environment outside the cell may be another cell or it may be the environment outside the suppository such as e.g. a mucous surfaces of a body cavity. Although a local environment of the composition may thus contain such open, cells, the local environment may be surrounded partly or wholly by a number of closed cells, or surrounded by and contained in a biocompatible polymer. This may be advantageous when a desirable flexibility of the polymer composition is needed. Such cells will be termed open, non-accessible cells, as the cells are not accessible to liquid or moisture provided by an external environment such as e.g. moisture secreted from or released by mucous surfaces of a body cavity.

In addition to non-accessible, open cells that are e.g. air-filled, but not accessible to moisture secreted from mucous surfaces of a body cavity, the polymer composition may also contain open cells, or at least a portion of open cells that are interconnected and accessible to e.g. moisture secreted from mucous surfaces of a body cavity. This is particularly important when it is desirable to attract an operable contact between e.g. a medicament comprised in such open, accessible cells of the polymer composition, and a mucous surface of a body cavity through which the medicament is to be taken up.

It should be noted that the suppository according to the invention solves two technically related problems at the same time. Firstly, the suppository according to the invention, is capable of releasing a bioactive substance to a predetermined, local environment of a mucousal membrane essentially without any of the systemic effects observed due to melting of traditional suppositories. Secondly, the suppository according to the invention does not cause irritation of the mucousal membranes. This latter effect is achieved by regulating the uptake of moisture into the suppository according to the invention in such a way that enough moisture is taken up so as to ensure sufficient release of bioactive substance, such as a medicament to provide delivery to the mucousal membrane of a pharmaceutically effective dose without causing irritation of the mucousal membrane due to an excessive dehydration caused by "drying out" the mucousal membrane when it is contacted by the suppository according to the invention.

The technical effect is achieved by carefully combining a number of parameters selected from the group consisting of i) the surface properties of the biocompatible polymer, ii) the "pore" size of the accessible, open cells, and iii) an optional layer or coating further controlling the moisture permeability of the suppository, and iv) an optional encapsulation of the medicament aiding the release of the medicament and the subsequent contact between the medicament and the mucousal membrane.

In one embodiment there is provided a polymer composition comprising both open cells and closed cells, wherein the majority of the cells are open cells, such as a polymer composition wherein more than about 80% of the cells are open cells, for example more than 85% open cells, such as 90% open cells, for example 92%, such as a polymer composition wherein more than about 94% of the cells are open cells, for example more than 96% open cells, such as 97% open cells, for example 98%, such as a polymer composition wherein more than about 99% of the cells are open cells, for example more than 99.5% open cells, such as 99.9% open cells, for example a polymer composition wherein essentially all the cells are open cells. The above indications of a majority of open cells pertain equally well—in different embodiments of the composition—to open, non-accessible cells, and open, accessible cells, within the definitions of these terms provided herein above. It is preferred that the polymer composition comprises more than 99% open, accessible cells.

In one embodiment of the present invention the controlled release formulation is comprised within the open cells of the polymer composition. Almost every open cell or only a fraction of the open cells may comprise the controlled release formulation.

The biocompatible polymer is preferably a branched polymer with branching points suitable for generating a density and a compression modulus that is suitable for solving the technical problems solved by the present invention.

The biocompatible polymer may be a co-polymer comprising a first polymer and/or a second polymer, wherein at least part of one of the first and second polymer is branched or crosslinked to either one or both of the first and second polymer. This means that in one embodiment the first polymer may form a branched network that may optionally be crosslinked or otherwise attached to another network formed by a second polymer. In this way the polymer composition may further comprise a plurality of open cells at least partly separated from one another by an interpenetrating matrix comprising at least one biocompatible polymer in branched or crosslinked form.

In one embodiment the polymer composition according to the invention has a glass-rubber transition temperature of the biocompatible polymer above about 15° C. and preferably below 40° C., such as a glass rubber transition temperature in the range of about 20° C. to about 40° C., for example about 35° C., such as about 36° C., for example in the range of about 20° C. to about 36° C., such as in the range of about 22° C. to about 36° C., for example in the range of about 24° C. to about 36° C., such as in the range of about 26° C. to about 36° C. for example in the range of about 27° C. to about 36° C., such as in the range of about 28° C. to about 36° C. for example in the range of about 29° C. to about 36° C., such as in the range of about 30° C. to about 36° C. for example in the range of about 31° C. to about 36° C., such as in the range of about 32° C. to about 36° C., for example in the range of about 33° C. to about 36° C., such as in the range of about 34° C. to about 36° C. for example in the range of about 34.5° C. to about 36° C., such as in the range of about 35° C. about 36° C. In another embodiment the polymer composition according to the invention has a glass-rubber transition temperature of the biocompatible polymer below 15° C. and preferably above −40° C., such as a glass rubber transition temperature in the range of about −30° C. to about −10° C., for example about −25° C., such as about −15° C. for example in the range of about −20° C.

In a further embodiment there is provided a suppository having a compression modulus of a first value, such as e.g. about 25 kPa, at first temperature, such as e.g. 25° C., for example 26° C., such as 27° C., for example 28° C., such as 30° C., add another compression modulus of a second and lower value, such as e.g. less than 25 kPa, for example 20 kPa, such as 15 kPa, at a second and higher temperature, such as e.g. 32° C., for example 33° C., such as 34° C., for example 35° C., such as 36° C. Preferred values are about 25 kPa at about 30° C., and about 20 kPa at about 36° C. The above approximate values ensure firstly that a suppository according to the invention can be inserted into a body cavity relatively easily and without causing any great pain to the individual, while adopting a more flexible and less rigid structure when positioned in the body cavity.

The same technical effect can be achieved by providing the suppository with an inner core of a relatively rigid material, and an outer portion or surrounding part comprising a polymer composition that is more flexible and less rigid. The outer portion typically has a lower compression modulus value. In one preferred embodiment the inner core consists of a retraction means extending axially through the suppository. The retraction means preferably is a rod or a piece of string capable of providing the required rigidity to the suppository.

The biocompatible polymer may be any polymer that does not attract an acute phase response, i.e. any polymer generally recognised as being safe for contacting human or animal tissue or skin. The polymer is preferably selected from the group consisting of polyurethanes, polyethylenes, and polypropylenes, and more preferably the polymer is polyurethane, such as a polyurethane comprising at least one polyisocyanat that is at least partly polymerised with at least one polyol, and preferably a polyurethane wherein essentially all of the at least one polyisocyanat is polymerised with essentially all of the at least one polyol.

The at least one polyisocyanat is preferably selected from the group consisting of aromatic polyisocyanates, aliphatic polyisocyanates, and heterocyclic polyisocyanates, and the at least one polyol is preferably and independently thereof selected from the group consisting of aromatic polyols, aliphatic polyols, and heterocyclic polyols.

Conceivable and preferred suppositories according to the invention comprise one or more of i) polymer compositions wherein the at least one polyol is aliphatic and wherein the at least one polyisocyanat is aliphatic, ii) polymer compositions wherein the at least one polyol is aliphatic, such as a polymer comprising or essentially consisting of repeating units of 2,2-dihydroxy-dipropylether, and wherein the at least one polyisocyanat is aromatic, such as a polymer comprising or essentially consisting of repeating units of diphenylmethandiisocyanat, iii) polymer compositions wherein the at least one polyol is aromatic, and wherein the at least one polyisocyanat is aliphatic, and iv) polymer compositions wherein the at least one polyol is aromatic, and wherein the at least one polyisocyanat is aromatic.

The polymer compositions may comprise more than one polyol, such at two polyols, for example three polyols, and more than three polyols. The polyol is preferably selected from the group consisting of diols and triols, and preferably polyols such as diols and/or trials having an average functionality of between 0.2 and 5, such as an average functionality of between 0.5 and 2, for example an average functionality of between 0.6 and 1.5. The ratio of i) NCO groups contained the at least one polyisocyanate to ii) OH groups contained in the at least one polyol, respectively, is in one embodiment preferably within the range of from about 0.5 to about 2.5, and preferably within the range of about 0.7 to about 1.3.

In another embodiment there is provided a suppository which may comprise i) a central core comprising a first composition, and ii) a surrounding part surrounding the central core and comprising a second composition.

In one preferred embodiment the central core comprises the controlled release formulation and the surrounding part comprises the polymer composition.

In another embodiment the central core comprises the polymer composition and the surrounding part comprises the controlled release formulation.

However, it is also possible that the first composition comprises at least one biocompatible polymer that is essentially non-biodegradable and wherein the first composition does not swell when contacted with an aqueous fluid, and the second composition comprises at least one biocompatible polymer that is essentially non-biodegradable and wherein the second composition does not swell when contacted with an aqueous fluid, and wherein the first composition is not identical to the second composition.

It is preferred that the density of the central care, measured as mass per unit volumes is higher than the density of the surrounding part, measured as mass per unit volume, however, the density of the central core and the surrounding part may be dependent on temperature. In that case the density of the central core, measured as mass per unit volume, is preferably higher than the density of the surrounding part measured as mass per unit volume at a specific predetermined temperature, such as for example a temperature between 0° C. and 25° C.

The suppository may further comprise a peripheral part comprising a third composition that is not identical to any of said first and second compositions, and wherein at least part of the third composition is in contact with the surrounding part comprising the second composition. The peripheral part is preferably a layer controlling water influx into the suppository by defining a barrier between the suppository and fluid present in an external environment that is in contact with the suppository under practical circumstances.

The suppository may further comprise a coating composition for coating at least the polymer composition comprising the at least one biocompatible polymer, wherein the coating composition covers at least part of the surface area of said polymer composition comprising the at least one biocompatible polymer, and wherein the coating composition is not identical to the polymer composition comprising the at least one biocompatible polymer.

The controlled release formulation according to the present invention may be any formulation, which is capable of releasing a bioactive substance in a controlled manner and which at least comprises:

i) at one first polymer ii) at least one second polymer wherein the melting point of the at least one first polymer is lower than the melting point of said at least one second polymer.

Preferably, the controlled release formulation is preferably solid at low temperatures, e.g. temparatures of less than 25° C., while being soft at higher temperatures, e.g. temperatures of more than e.g. 30° C. Accordingly, the controlled release formulation preferably has a softening point so that the suppository is essentially rigid at room temperature, while the suppository is essentially soft or at least less rigid at body temperature.

The advantages of such a softening point are several. Firstly, it is easier to insert a suppository into a body cavity when it is rigid or solid. Secondly, once inserted a soft suppository may adapt to the shape of the body cavity wherein i is inserted, which make it more confortable to carry and enables better contact between the suppository and the mucosal membrane of the body cavity.

Preferably, the controlled release formulation has a softening point between 15° C. and 45° C., more preferably, the controlled release formulation has a softening point between 25° C. and 40° C., even more preferably, the controlled release formulation has a softening point between 30° C. and 35° C. For example, the controlled release formulation may have a softening point from 20° C. to 25° C., such as from 25 to 30° C., for example around 31° C., such as around 32° C. for example around 33° C., such as around 34° C., for example around 35° C., such as around 36° C., for example around 37° C., such as between 37° C. and 40° C., for example between 40° C. and 45° C.

In one embodiment of the present invention the controlled release formulation comprises two different first polymers. However, the controlled release formulation may also comprise more than two different first polymers, such as for example 3, for example 4, such as 5, for example 6, such as 7, for example 8,such as 9, for example 10, such as more than 10 different first polymers.

The first polymers of the controlled release formulation according to the present invention may be any polymer suitable for the manufactory of a controlled release formulation. Preferably, the first polymer has a melting point below 50° C., more preferably, below 45° C. For example the melting point of the first polymer may be between 40° C. and 45° C., such as between 35° C. and 40° C., for example between 30° C. and 35° C., such as between 25° C. and 30° C., for example between 20° C. and 25° C., such as between 15° C. and 20°, for example between 10° C. and 15° C., such as between 5° C. and 10°, for example between 0° C. and 5° C., such as lower than 0° C.

In one preferred embodiment the first polymer of the controlled release formulation is selected from the group consisting of polyethylenglycols (PEG). PEGs are a group of liquid or solid polymers of the general formula $H(OCH_2CH_2)_nOH$.

Preferably, the first polymer is a PEG, which has an average molecular weight of between 100 and 1500, more preferably, the PEG has an average molecular weight of between 400 and 1000. For example, the first polymer may be a PEG, which has an average molecular weight of around 100, such as around 200, for example around 300, such as around 400, for example around 500, such as around 600, for example around 700, such as around 800, for example around 900, such as around 1000, for example around 1100, such as around 1200, for example around 1300, such as around 1400, for example around 1500.

In another example, the first polymer may be a PEG with an average n value of between 4 and 6, such as between 6 and 8, for example between 8 and 10, such as between 10 and 12, for example between 12 and 14, such as between 14 and 16, for example between 16 and 18, such as between 18 and 20, for example between 20 and 22, such as between 22 and 24, for example between 24 and 26, such .as between 26 and 28, for example between 28 and 30, such as between 30 and 32, for example between 32 and 34, such as between 34 and 36. Preferably, the average n value is between 8.2 and 9.1 or between 20 and 25.

In one preferred embodiment, the first polymer may be a PEG that has an average molecular weight of around 400. In another preferred embodiment, the first polymer may be a PEG that has an average molecular weight of around 1000.

In one embodiment of the present invention the controlled release formulation comprises two different second polymers. However, the controlled release formulation may also comprise more than two different second polymers, such as for example 3, for example 4, such as 5, for example 6, such as 7, for example 8,such as 9, for example 107 such as more than 10 different first polymers.

The second polymers of the controlled release formulation according to the present invention may be any polymer suitable for the manufactory of a controlled release formulation. Preferably, the first polymer has a melting point above 20° C., more preferably, above 25° C., even more preferably above 30° C. For example the melting point of the first polymer may be between 20° C. and 25° C., such as between 25° C. and 30° C., for example between 30° C. and 35° C., such as between 35° C. and 40° C., for example between 40° C. and 45° C., such as between 45° C. and 50°, for example between 50° C. and 55° C., such as between 55° C. and 60°, for example between 60° C. and 65° C., such as above than 65° C.

In one preferred embodiment the second polymer of the controlled release formulation is selected from the group consisting of polyethylenglycols (PEG).

Preferably, the second polymer is a PEG, which has an average molecular weight of more than 1000, more preferably between 1000 and 35,000, even more preferably, the PEG has an average molecular weight of between 1500 and 10,000. For example, the second polymer may be a PEG, which has an average molecular weight of around 1000, such as around 2000, for example around 3000, such as around 4000, for example around 5000, such as around 6000, for example around 7000, such as around 8000, for example around 9000, such as around 10000. for example around 11000, such as around 12000, for example around 13000, such as around 14000, for example around 15000.

In another example, the second polymer may be a PEG with an average n value of between 20 and 25, such as between 25 and 30, for example between 30 and 35, such as between 40 and 50, for example between 50 and 60, such as between 60 and 80, for example between 80 and 100, such as between 100 and 125, for example between 125 and 150, such as between 150 and 175, for example between 175 and 200, such as between 200 and 250, for example between 250 and 300, such as between 300 and 400, for example between 400 and 600, such as between 600 and 1000, for example more than 1000. Preferably, the average n value is between 68 and 84 or between 158 and 204.

In one preferred embodiment, the second polymer may be a PEG that has an average molecular weight of around 2000. In another preferred embodiment, the second polymer may be a PEG that has an average molecular weight of around 4000. In yet another preferred embodiment, the second polymer may be a PEG that has an average molecular weight of around 6000.

Thus, it is preferred according to the present invention that the controlled release formulation comprises a first polymer, which is selected from the group consisting of PEG with an average molecular weight of between 200 and 1500 and a second polymer, which is selected from the group consisting of PEG with an average molecular weight of between 1000 and 35,000.

In one particularly preferred embodiment, the first polymer is PEG with an average molecular weight around 1000 and the second polymer is PEG with an average molecular weight around 4000.

The ratio between the first polymer and the second polymer may be chosen dependent on the nature of the first and the second polymer, to obtain a controlled release formulation with a suitable softening point. For example, the ratio between first polymer and second polymer may be around 100:1, such as around 95:1, for example around 90:1, such as around 85: 1, for example around 80:1, such as around 75:1, for example around 70:1, such as around 65:1, for example around 60:1, such as around 55:1, for example around 50:1, such as around 45:1, for example around 40:1, such as around 35:1, for example around 30:1, such as around 25:1, for example around 20:1, such as around 18:1, for example around 16:1, such as around 14:1, for example around 12:1, such as around 10:1, for example around 9:1, such as around 8:1, for example around 7:1, such as around 6:1, for example around 5:1, such as around 4:1, for example around 3:1, such as around 2:1, for example around 1:1.

Alternatively, the ratio between second polymer and first polymer may be around 100:1, such as around 95:1, for example around 90:1, such as around 85:1, for example around 80:1, such as around 75:1, for example around 70:1, such as around 65:1, for example around 60:1, such as around 55:1, for example around 50:1 such as around 45:1, for example around 40:1, such as around 35:1, for example around 30:1, such as around 25:1, for example around 20:1, such as around 18:1, for example around 16:1, such as around 14:1, for example around 12:1, such as around 10:1, for example around 9:1, such as around 8:1, for example around 7:1, such as around 6:1, for example around 5:1, such as around 4:1, for example around 3:1, such as around 2:1, for example around 1:1.

Preferably, the ratio between second polymer and first polymer is between 3:1 and 10:1.

However, it is also contained within the present invention to use more than one first polymer and/or more than one second polymer, which may be mixed in any ratio suitable to obtain a softening point around 25° C. to 45° C.

In one embodiment of the present invention, the controlled release formulation furthermore comprises a surface active agent. For example the surface active agent may be a PEG monoester, such as for example a PEG monostearate.

In a particular preferred embodiment the controlled released formulation according to the inventon comprises at least one bioactive substance, wherein the bioactive substance preferably may be a medicament. The medicament according to the present invention may be any medicaments for example the medicaments mentioned herein above. In one embodiment of the present invention the medicament is an analgetic, for example lidocain.

The medicament may be provided in any one or more of i) a central part of the suppository comprising a first composition ii) a surrounding part comprising a second composition, said surrounding part surrounding the central part, iii) a peripheral part comprising a third composition, wherein at least a portion of said peripheral part including a surface area is contacting the surface area of the surrounding part of the suppository, and iv) a coating composition the surrounding part of the suppository and/or the peripheral part of the suppository.

The first composition and/or second compostions and/or third composition may be polymer composition or a controlled release formulation. Preferably, when comprising a medicament the first composition and/or second composition and/or third composition is a controlled release formulation.

A suppository comprising any one or more of the above compositions will thus comprise a core part, and one or more layers at least partly encapsulating the core part and/or one or more parts layered onto the core part, wherein said layers are at least in pairwise contact with each other. The layers preferably contact each other at predetermined boundaries defining a transition phase clearly separating one composition form one or more of the other compositions.

The medicament may be comprised in the coating compostion, and may additionally also be comprised in the peripheral part of the suppository, and optionally also in the surrounding part of the suppository as well as further optionally also in the central part of the suppository comprising the at least one biocompatible polymer.

In another embodiment there is provided a suppository according to the invention comprising a medicament in the central part of the composition comprising the biocompatible polymer. Preferably, the central part is then a controlled release formulation. The medicament may additionally also be comprised in the surrounding part of the suppository, and optionally also in the peripheral part of the suppository, and further optionally the medicament may also be comprised in the coating composition coating either the surrounding part or the peripheral part of the suppository.

The suppository may comprise more than one bioactive substance, such as more than one medicament, such as two medicaments, for example three medicaments, and the plurality of medicaments may be comprised in the same or different parts of the suppository depending on the preferred method of administration, be it sequentially, in any order, or essentially simultaneously. The suppository can be manufactured to accomplish for special needs in respect of administration of medicament It is also possible to change the suppository at suitable intervals, such as e.g. every 4 to 12 hours, for example 5–12 hours, such as 6–12 hours, for example 7–12 hours, such as 8–12 hours, for instance 9–12 hours such as 10–12 hours, for example 5–11 hours such as 5–10 hours for example 5–9 hours such as 5–9 hours, for example 5–8 hours such as 5–7 hours, for example 6–11 hours such as 7–10 hours, for example 8–9 hours, without causing any pain to the individual being treated. The change will sustain an administration of the medicament to a local environment.

It is particularly preferred that the medicament may be controllably releasable. Preferred controlled release formulations are mentioned herein above. However, the medicament may also be controllably released by means of being encapsulated in capsules comprising at least one encapsulation agent, preferably an encapsulation agent selected from the group of encapsulation agents consisting of PEG, any protein and any lipids. Pegylated (PEG-coated) medicaments are one preferred example of encapsulated medicaments capable of being administered according to the present invention. Medicament comprising capsules may either disintegrate or dissolve in order to release the medicament.

In another preferred embodiment, the present invention relates to a suppository comprising at least one polymer composition wherein the polymer composition comprises at least one biocompatible polymer, which is essentially non-biodegradable, wherein the suppository essentially does not swell when contacted with an aqueous fluid, and wherein the suppository comprises a controlled release formulation comprising at least one medicament that is dispersed, preferably substantially homogeneously dispersed, in the controlled release formulation and/or located in at least one geometrically well-defined zone within a controlled release formulation, wherein said controlled release formulation is capable of releasing the medicament into an aqueous phase by erosion of at least one surface of the controlled release formulation, preferably an erosion that takes place at a substantially constant rate under practical conditions.

Preferred controlled release formulations according to the present invention are described herein above. However, alternatively the controlled release formulation according to the invention may comprise i) a matrix of a substantially water soluble crystalline polymer, or a mixture of substantially water soluble crystalline polymers, ii) a surface active agent, or a mixture of surface active agents, dispersed in the crystalline polymer phase in an amount of from 0 to about 50% by weight of the crystalline polymer and the surface active agent,
wherein the surface active agent comprises a) a compound or compounds having at least one domain which is compatible with the crystalline polymer phase and b) at least one other domain which is substantially lipophilic, and
wherein the surface active agent has a melting point lower than that of the crystalline polymer, or the mixture of substantially water soluble crystalline polymers, iii) at least one bioactive substance, such as for example a medicament substantially homogeneously dispersed in the crystalline polymer phase and/or dispersed in the surface active agent and/or located in geometrically well-defined zones within the composition, and optionally iv) a filler.

The surface active agent and/or the medicament reduces the water affinity of domains between grains and in cracks in the crystalline polymer matrix and in the crystalline polymer matrix itself, thereby reducing or substantially eliminating water diffusion in the interface between the polymer crystals. In one embodiment, the erosion is predominantly effected by the dissolving action of an aqueous medium on a surface or surfaces of the suppository exposed to the medium.

The combination of the matrix and the medicament and/or the surface active agent must be substantially impenetrable to fluids of the aqueous phase, for example body fluids present where e.g. a suppository comprising the controlled release formulation according to the invention is introduced into a body cavity, including the rectum and the vagina, in order to eliminate or reduce degradation of the medicament residing in the matrix due to the action of water, This is particularly relevant when the medicament is susceptible to hydrolysis.

The inclusion of the medicament into a matrix into which water diffusion is substantially eliminated will thus impart stability to the controlled release formulation, so that the medicament will remain active even when the controlled release formulation has been exposed to body fluids or other fluids for the predetermined time.

As the fluids may in one embodiment of the present invention act only on the surface of a matrix, the medicament embedded therein is only exposed to the fluids in question when it is released or immediately prior to its release from the matrix. A matrix of a type which is substantially non-permeable to water will therefore ensure the stability of the medicament in the matrix for the entire period of time when the controlled release formulation is present in the aqueous phase, for example a body cavity, until the time when the medicament is released. This will also facilitate or result in a controlled and reproducible release rate of the medicament from the matrix, as the release of the medicament proceeds gradually from the surface or surfaces of the matrix that is exposed to the fluids in question.

Different geometries of surfaces will naturally lead to different release rates, and it is preferred in one embodiment that the release rates—although variable in terms of time and released amounts in accordance with the individual design and geometry of the matrix—are at least substantially reproducible under practical conditions for a particular design and geometry of the matrix and/or the surface. The term "controlled release" does in no way preclude that different amounts of medicament is released over time, provided that the geometry and design of the matrix and/or the surface is intended for this purpose. An example of such a variable, controlled release is an initial "booster" release of a relatively high amount of medicament, followed by a subsequent "steady state" release of amounts of medicament that are substantially unchanged per time unit. However, it may also be possible to exploit a design wherein substantially all of the medicament, or a part thereof, is released in a "steady state" mode characterised by a release of medicament that is substantially unchanged per time unit.

Time units are preferably measured in hours or minutes, such as from several hours to a few minutes, such as time units in the order of from 4 to 6 hours, such as 6 hours, for example 5 hours, such as 4.5 hours; for example 4 hours, such as 3.5 hours, for example 3 hours, such as 2.5 hours, for example 2 hours, such as 1.5 hours, for example 1 hour.

Accordingly, it is also possible to calculate time units in minutes, such as from only a few minutes to about 60 minutes, including time units in the order of from 2 to 60 minutes, such as 55 minutes, for example 45 minutes, such as 40 minutes, for example 35 minutes, such as 30 minutes, for example 25 minutes, such as 20 minutes, for example 15 minutes, such as 10 minutes, for example 5 minutes, such as 2 minutes.

The rate at which the medicament is released from the matrix is in one preferred embodiment a predetermined rate, i.e. a rate which is controllable over a certain period of time as indicated herein immediately above. The release rate required in each particular instance may inter alia depend on the amount of medicament to be released for it to exert the desired effect, as well as on the overall dosage of the medicament contained in the matrix. The substance of which the matrix is composed and the distribution of the medicament in the matrix may therefore be selected according to one or more of these criteria to ensure the desired level of release of the medicament.

The controlled release formulation according to the invention has the advantage that the dosage of the medicament included in the matrix may be measured so that an appropriate constant or pulsatile dosage thereof will be available in the aqueous phase for the entire period of time that the controlled release formulation is present in the aqueous phase; the nature of the matrix structure, i.e. its water-impenetrability, prevents degradation by hydrolysis or other means of the medicament due to diffusion of water into the matrix even if the medicament in itself is unstable in an aqueous environment.

In one embodiment of the invention and due to the controlled release of the medicament, it is possible to obtain a substantially constant rate of release or a controlled pulsatile release of the medicament over a specific period of time, corresponding to the dosage necessary for the treatment in question. In this way, adherence to a strict dosage regimen, e.g. requiring administration of a medicament at set intervals up to several times a day, may be dispensed with.

Furthermore, it is possible to include two or more different medicaments in the controlled release formulation according to the invention, adapted to be released at different concentrations and/or intervals, thus making it easier for patients to follow a prescribed regimen.

The controlled release formulation according to the invention allows for the incorporation of high concentrations of the medicament relative to the size of the controlled release formulation. This is an advantage, notably when the controlled release formulation is to be used for the delivery of a medicament, as it allows for the delivery of the required amount of the medicament without the volume of the controlled release formulation being unnecessarily large.

Additionally, sparingly soluble or non-soluble medicaments may be readily incorporated into the controlled release formulation according to the invention, since such substances are compatible with the lipophilic domains of the surface active agent. The controlled release formulation according to the invention may thus be used for the delivery of, for example, sparingly soluble or non-soluble pharmaceutical powders which can otherwise be difficult to administer When matrix of the controlled release formulation comprises a substantially water soluble crystalline polymer or a mixture of substantially water soluble crystalline polymers, a surface active agent will typically be dispersed in the crystalline polymer phase. The surface active agent preferably comprises a compound or compounds having at least one domain which is compatible with the crystalline polymer phase and at least one other domain which is substantially lipophilic.

The term "compatible", as used in the context according to the invention, refers to the fact that the surface active agent is able to become emulsified in the melted polymer, as explained below. The surface active agent preferably has a substantially hydrophilic domain which gives it affinity to the crystalline polymer phase, thereby filling in domains between grains and in cracks in the crystalline polymer matrix, and preferably also a substantially lipophilic domain capable of reducing the water affinity in the interfaces between the grains and in the cracks in the crystal structure. The result of this action is a reduction and/or a substantial elimination of water diffusion into the interface present between polymer crystals.

The above-mentioned cracks and grains in the crystalline polymer matrix may be a result of the process in which the crystals are formed. During the crystallization process, the matrix may shrink and this tends to form cracks and imperfect zones between the crystal grains. Accordingly, the surface active agent should preferably be mobile even after the polymer material of the matrix has solidified and formed crystals. Therefore, the melting point of the surface active agent in one embodiment is lower than that of the crystalline polymer phase.

It is preferred that a substantially homogenous distribution of the surface active agent can be obtained in the melted polymer prior to crystallizaton. Thus, the surface active agent should preferably be capable of becoming emulsified in the melted polymer.

It has been found that substantially hydrophobic medicaments tend to result in a decrease in the erosion rate of the controlled release formulation. Substantially hydrophilic or water-soluble medicaments have been shown to have the opposite effect, i.e. they tend to result in a faster erosion of the matrix. It has furthermore been found that if the controlled release formulation is prepared without an medicament, the controlled release formulation will tend to erode at a relatively fast rate.

The degree of dispersion of the surface active agent in the matrix seems to be important for the erosion rate of the matrix, a more uniform dispersion resulting in a slower erosion rate. It is thus believed that substantially hydrophobic medicaments tend to lead to a more uniform dispersion of the surface active agent, thereby leading to a decreased erosion rate of the matrix, while nonhydrophobic medicaments have the opposite effect.

When the controlled release formulation is prepared with a medicament which is not substantially hydrophobic, or when the content of the medicament in the controlled release formulation is relatively low, it may therefore be desirable to add one or more fillers in order to modify the dispersion of the surface active agent and reduce the erosion rate of the matrix It is believed that the addition of a filler serves to increase the viscosity of the mixture, whereby the surface active agent becomes more uniformly dispersed in the matrix. Examples of suitable fillers are dextrin, sucralfate, calcium hydroxyl-apatite, calcium phosphate and fatty acid salts such as magnesium stearate. The filler may be added in an amount so that the combination of the filler and the medicament comprises up to about 60%, typically up to about 50%, such as up to about 40% by weight of the controlled release formulation.

The surface active agent is typically a non-ionic emulsifier comprising one or more fatty acid esters and/or fatty acid ethers, for example a fatty acid ester and/or fatty acid ether having carbon chains of from 12 to 24 carbon atoms, typically from 12 to 20 carbon atoms, such as an ester and/or ether of palmitic acid or stearic acid. Typical surface active agents may comprise a polyglycol ester or ether, a polyethylene glycol ester or ether, a polyhydroxy ester or ether and/or a sugar ester or ether such as a sorbitan ester or ether. The surface active agent will suitably have an HLB (hydrophiliclic-lipophilic balance) value of from about 4 to about 16.

Furthermore, the surface active agent is preferably an emulsifier which is fysiologically and/or pharmaceutically acceptable. A preferred surface active agent is polyethylene glycol monostearate, in particular polyethylene glycol 400 monostearate Tartaric acid, citric acid and lactic acid esters of mono- and diglycerides, as well as fatty acid esters of glycerol, may also be employed as a surface active agent.

It may in certain cases be desirable to incorporate a mixture of surface active agents into the matrix, in order to improve the dispersion of the primary surface active agent in the matrix and reduce the erosion rate.

In some cases, the medicament itself will be capable of functioning as a surface active agent, i.e. it will have at least one domain which is compatible with the crystalline polymer phase and at least one other domain which is substantially lipophilic, so that the medicament alone will be capable of becoming substantially homogeneously dispersed in the crystalline polymer phase and substantially eliminating diffusion of water into the matrix. In this case, the role of the surface active agent, i.e. its function as a repair medium and as a surfactant, will be partially or completely fulfilled by the medicament itself, and little or no surface active agent may be required. Thus, when the medicament itself has properties of a non-ionic emulsifier, the surface active agent may be absent from the controlled release formulation or may be present in the controlled release formulation in an amount of, for example, about 0–2% by weight of the matrix.

When the medicament does not possess properties of a surface active agent, the surface active agent is typically present in the controlled release formulation in an amount of about 2–50%, e.g. about 5–50%, typically about 10–40%, more typically about 15–35%, such as about 20–30%, by weight of the crystalline polymer and surface active agent. As mentioned above, a surface active agent content of less than 2% may however be employed when the medicament possesses surface active agent properties.

Although a medicament content of about 60% is contemplated to be the maximum content which still allows for a sufficient content of the crystalline polymer matrix and the surface active agent in the controlled release formulation, the medicament may, on the other hand, be present in the controlled release formulation in much smaller amounts, depending on the nature and strength of the medicament in question.

A maximum surface active agent content of about 50%, depending on the nature of the surface active agent, the medicament and the crystalline polymer, as well as on the desired delivery characteristics of the controlled release formulation, will generally be sufficient in order to attain the desired effects associated with their presence.

The crystalline polymer matrix typically comprises a polyglycol, e.g. in the form of a homopolymer and/or copolymer. Preferred polymers are polyethylene glycols or block copolymers of ethylene oxide and propylene oxide.

Polyethylene glycols which are suitable for use in the crystalline polymer matrix are those having a molecular weight of from about 2000 to about 500,000 daltons, typically from about 5000 to about 100,000 daltons, more typically from about 10,000 to about 50,000 daltons, and especially from about 20,000 to about 35,000 daltons. A preferred polyethylene glycol is one which has a molecular weight of about 35,000 daltons.

Typical block copolymers may be comprised of up to about 30% by weight of the polypropylene oxide based block, and have a molecular weight of above about 5000 daltons, typically about 5000 to about 30,000 daltons, more typically about 8000 to about 15,000 daltons.

The crystalline polymer matrix must have a melting point which is above the temperature of the aqueous medium in which the controlled release formulation according to the invention is to be used. Thus, the polymer(s) employed in the matrix will suitably have a melting point of about 20° C. to 120° C., typically about 30° C. to about 100° C., more typically about 40° C. to 80° C., depending on the how the controlled release formulation is to be employed. In particular, when the controlled release formulation according to the invention is used for the delivery of a drug for human or veterinary use, the matrix will suitably have a melting point of about 40° to about 80° C.

The medicament to be delivered by the controlled release formulation according to the invention can be any active substance for human or veterinary use, including a vitamin or other nutritional supplement, a disinfectant, a deodorant or another substance to be administered continuously in an aqueous environment.

The presence of the surface active agent and/or the medicament in the crystalline polymer matrix will reduce the water affinity of domains between grains and in cracks in the matrix, thereby substantially eliminating water diffusion in the interface between the polymer crystals, so that the erosion is predominantly effected by the dissolving action of an aqueous medium on a surface or surfaces of the controlled release formulation exposed to the medium.

Diffusion of water into the controlled release formulation is in one preferred embodiment substantially limited to the surface layer of the matrix, whereby the matrix may be eroded at a substantially constant and pH-independent rate, provided that the surface area remains constant. As a result, the invention in one particular embodiment pertains to a substantially zero order release of the medicament.

The term "zero order" refers to the fact that the release rate of the medicament is substantially constant per time unit. In this embodiment, the medicament is substantially homogeneously distributed in the matrix. In the case of the medicament being located in geometrically well-defined zones within the matrix, the result of the constant erosion rate of the matrix will be a strictly controlled pulsatile release of the active ingredient, optionally in the form of an initial "booster" effect.

It is important to obtain a geometric form of the controlled release formulation that is suitable for achieving the above-mentioned controlled "zero order", or pulsatile release. Thus, in one preferred embodiment of the present invention, the controlled release formulation according to the invention has a geometric shape which enables a substantially constant surface area to become exposed during erosion of the matrix. It will be understood that the suppository according to the present invention may comprise a plurality of compartments, including open cells as defined herein, wherein each compartment comprises a controlled release formulation, wherein a substantially constant surface area is exposed during erosion of the matrix.

Accordingly, the suppository according to the present invention comprising e.g. a plurality of compartments, including open cells as defined herein, wherein each compartment may comprise a controlled release formulation, wherein each of the plurality of compartments has substantially constant surface area exposed during erosion of the matrix may be a suppository comprising the controlled release formulation in the shape of a cube or a rod, including a cylindrical rod.

Some capsules are adapted to disintegrate and release the medicament when contacting body tissue, including mucousal membranes preferably found in a body cavity, whereas other capsules comprising the medicament are adapted to disintegrate and release the medicament when being contacted by a fluid, including moisture secreted by body tissue, including mucousal membranes preferably found in a body cavity, and still other capsules comprising the medicament are adapted to dissolve and release the medicament when contacting body fluids or body tissue, including mucousal membranes preferably found in a body cavity.

The suppository may further comprise an additive selected from the group of preservatives, adjuvants, stabilisers, lubricants, and disintegraters or any combinations thereof. Pharmaceutically and physiologically acceptable additives are preferred.

In another aspect the present invention relates to a suppository comprising a polymer composition as described herein above. The suppository may adopt any shape or from suitable for a suppository, including oblong shapes and essentially cylindrical shapes. The suppository should preferably be rounded in shape and fit the body cavity for which it is designed, e.g. a rectal cavity, a vaginal cavity, a nasal cavity, and an otogenic cavity.

Figure 10:
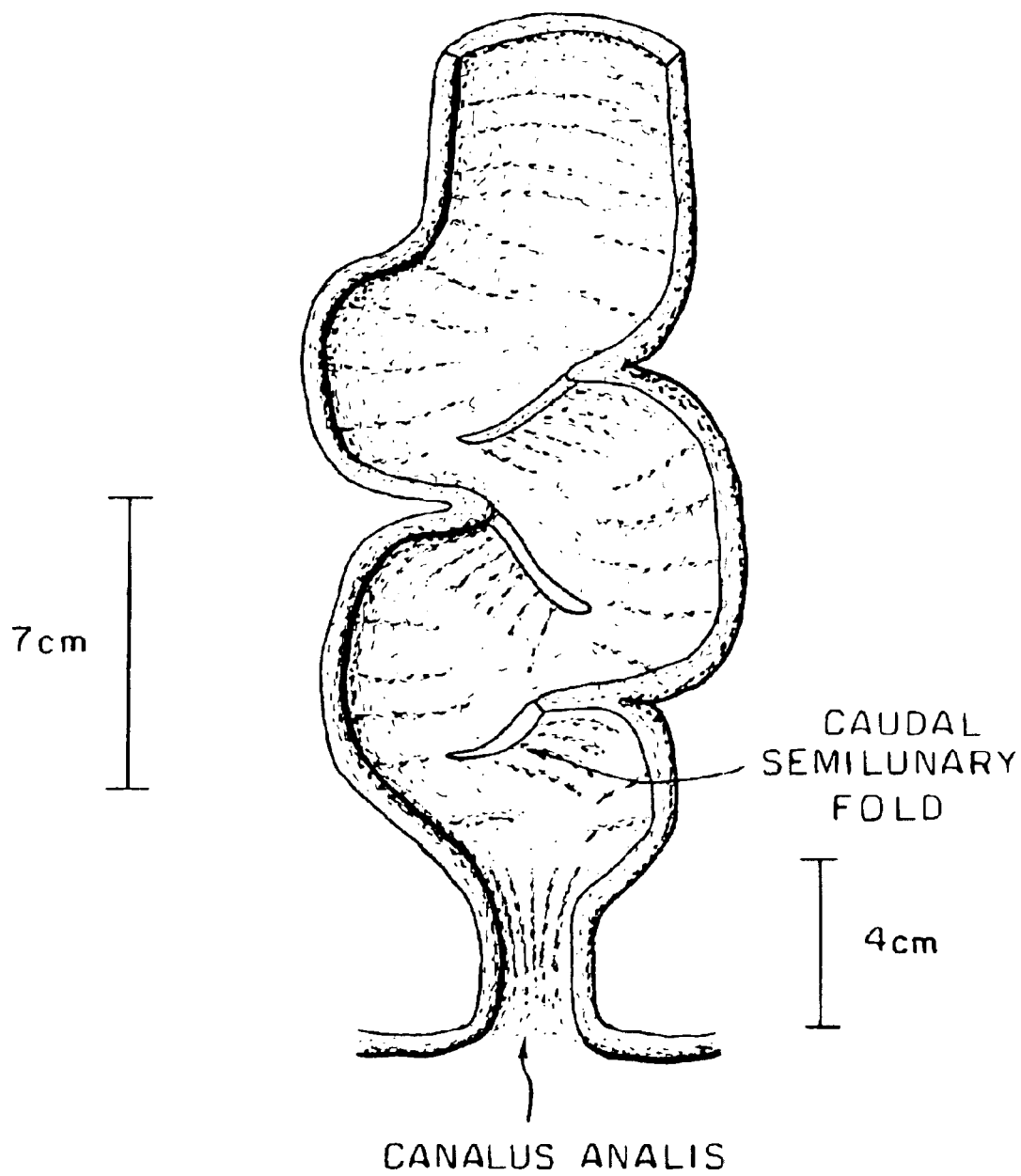
FIG. 10 illustrates a diagram of the rectum. The canalis analus and the caudal semilunary fold is indicated by arrow.

In one preferred embodiment the suppository has a shape that allows contact between parts of or essentially all of the outer surface of the suppository and parts of or essentially all of the mucosal membrane of the rectum below the caudal semilunary fold, when the suppository is situated in the rectum. Accordingly, the suppository can be used in any method for administration of a bioactive substance to e.g. the rectum, including the perineum, perirectal tissues and canalus analis. A diagram of the rectum showing the caudal semilunary fold and canalus analis is shown in FIG. 10. Contact between the outer surface of the suppository and the mucosal membrane preferably allows and/or promotes contact between the bioreative substance of the suppository and the mucosal membrane.

In another embodiment the suppository has a shape that allows contact between parts of or essentially all of the outer surface of the suppository and parts of or essentially all of the mucosal membrane of the vulva or vagina.

The suppository comprises a central portion, a first end portion and a second end portion, wherein, for certain preferred embodiments and uses, at least one of said end portions is tapering, and preferably pointed, with a rounded tip.

In another embodiment the suppository has a cylinder shaped central portion, a tapering, preferably pointed, distal end portion having a rounded tip, and a proximal end portion attached to a flange portion extending outwardly in the axial direction from said proximal end portion. In a particularly preferred embodiment the tapering distal end portion has a maximum diameter closest to the central portion that is larger than the average diameter of the central portion.

Figure 1B:
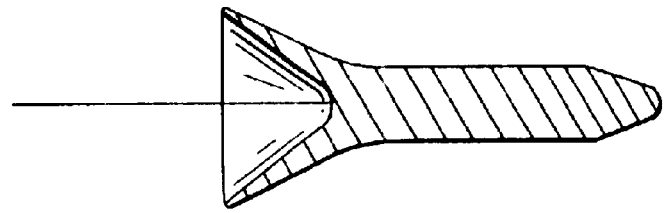

The suppository in another preferred embodiment has a central portion, a tapering, preferably pointed, distal end portion having a rounded tip, and a proximal end portion attached to a flange portion extending outwardly in the axial direction from said proximal end portion. In a particularly preferred embodiment the tapering distal end portion has a maximum diameter closest to the central portion that is larger than the average diameter of the central portion. This is illustrated in FIG. 1. This feature serves as an anchor and keeps the suppository in place during use.

The flange portion when present preferably has a recessed part in the axial direction, and the outer diameter of the flange portion is larger than the diameter of the central portion. This is also illustrated in FIG. 1.

The suppositories according to the present invention may be tested using a plurality of test methods. For example they may be tested by the test methods described in European Pharmacopoeia 2001 or USP or in other prior art litterature.

The suppositories may for example be tested by.

a) Uniformity of content b) Disintegration test c) Hardness testing using a penetrometer d) Melting test e) Modified tablet disintegration/fracture point testing, wherein the suppository is placed in a plastic container with water.

The present invention further pertains to a suppository according to the invention for use in a method of therapeutic treatment, including a method of surgical treatment, such as rectal surgery, and a suppository according to the invention for for use in a method of cosmetic treatment. There is also provided a suppository for use in a diagnostic method In a further aspect there is provided a method for preparation of a suppository according to the present invention, said method comprising the steps of i) providing starting materials suitable for polymerisation, ii) providing at least one first polymer and/or at least one second polymer for the preparation of a controlled release formulation and a bioactive substance iii) mixing the at least one first polymer and/or the at least one second polymer and the bioactive substance iv) mixing and polymerising said starting materials in a predetermined shape desirable for a suppository, thereby obtaining a biocompatible polymer in he shape desirable for a suppository v) contacting the biocompatible polymer with the mixture of the at least one first polymer, the at least one second polymer and the bioactive substance.

The biocompatible polymer may be shaped in a shape desirable for a suppository by any convenient method known to the person skilled in the art.

For example the suppository may be shaped by cast moulding or by extrusion.

Furthermore, the suppository may be shaped by means of injection moulding into a predetermined shape, and the starting materials preferably comprise at least one polyisocyanate and at least one polyol. There is also provided a suppository obtainable by the above method of manufacturing.

In further embodiments there is provided the use of a suppository according to the invention for treatment of one or more of conditions including pains, anaesthetic, epistomi, ruptured vagina, ruptured colon, rectal surgery, haemorrhoids, immunisation, cancer, hormonal treatment, and contraception.

There is also provided the use of a suppository according to the invention in the manufacture of a medicament for the treatment of one or more conditions including pains, anaesthetic, epistomi, ruptured vagina, ruptured colon, rectal surgery, haemorrhoids, immunisation, cancer, hormonal treatment, and contraception.

Further embodiments pertain to a method of therapeutic treatment comprising the step of bringing a suppository according to the invention into contact with body tissue including a mucousal membrane of a body cavity of an animal, including man, a method of surgical treatment comprising the step of bringing a suppository according to the invention into contact with body tissue including a mucousal membrane of a body cavity of an animal, including man, and a diagnostic method comprising the step of bringing a suppository according to the invention into contact with body tissue including a mucousal membrane of a body cavity of an animal, including man, and a method of cosmetic treatment comprising the steps of bringing a suppository according to the invention into contact with body tissue including a mucousal membrane of a body cavity of an animal, including man.

In a further embodiment there is provided the use of a biocompaticle polymer in the manufacture of a suppository according to the invention.

DESCRIPTION OF THE FIGURES

When intended for use as a rectal suppository the shapes and dimensions of suppositories according to preferred embodiments of the invention are approximately as illustrated in FIGS. 1, 5, 7, 8 and 9.

The overall length in the axial direction (the direction from the distal end portion to the proximal end portion), including the flange portion, is about 7.0 cm to 7.5 cm, the maximum diameter of the tapering distal end portion is about 1.4 cm to 1.8 cm, the average or minimum diameter of the central portion is about 0.9 cm to 1.1 cm, and the maximum diameter of the flange portion—at its proximal end—is about 1.2 cm to 2.5 cm.

Figure 6:
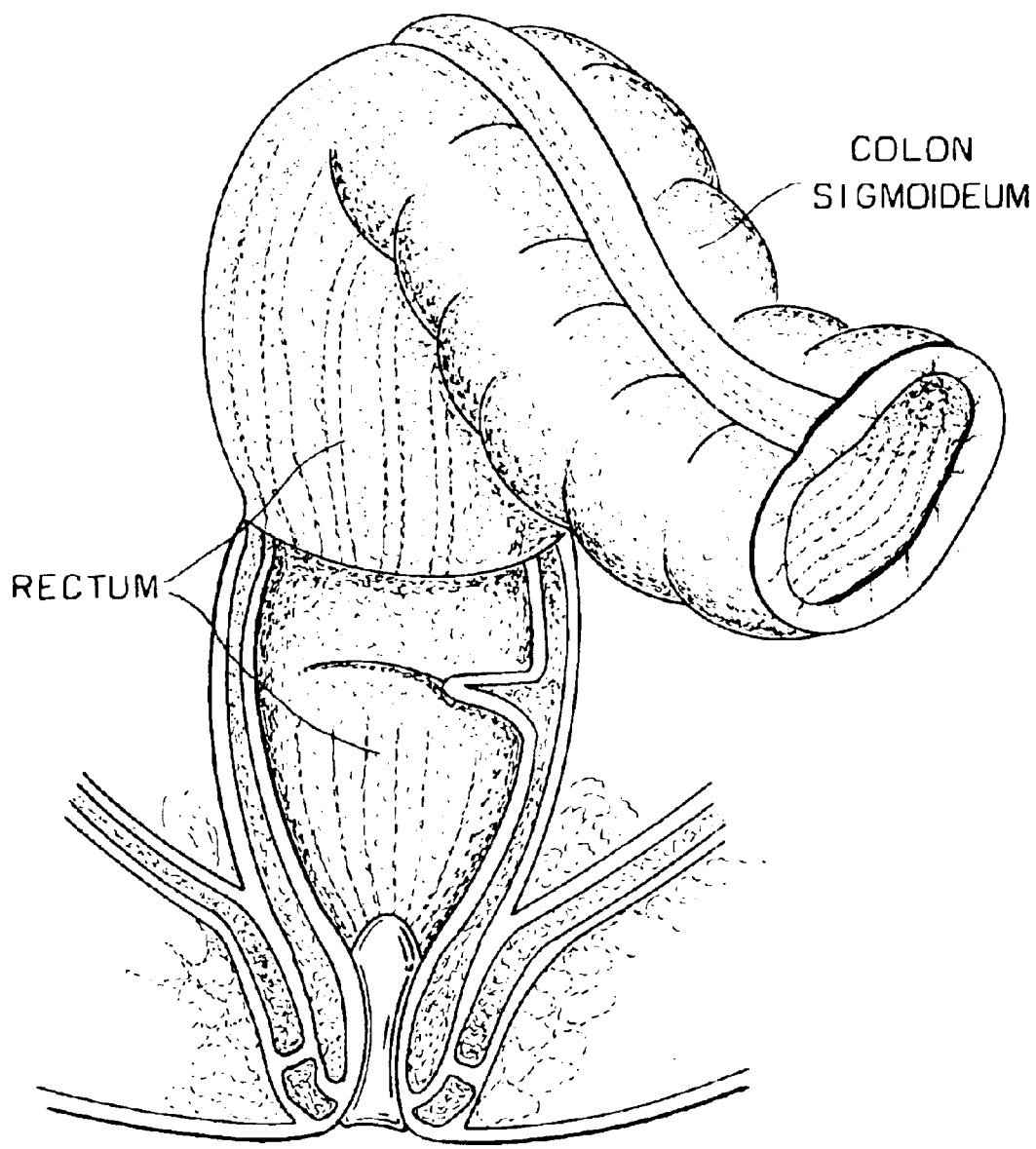
FIG. 6. Diagram of rectum showing the approximate location of a rectal suppository (black object).
Figure 7A:
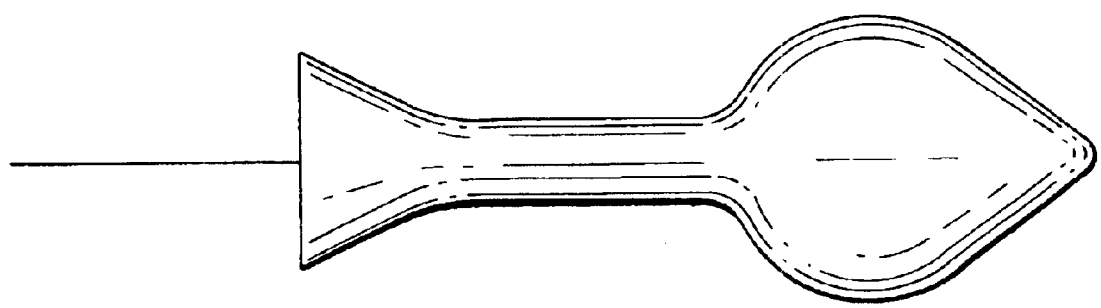
FIG. 7 Example of suitable shape of a rectal suppository
Figure 7B:
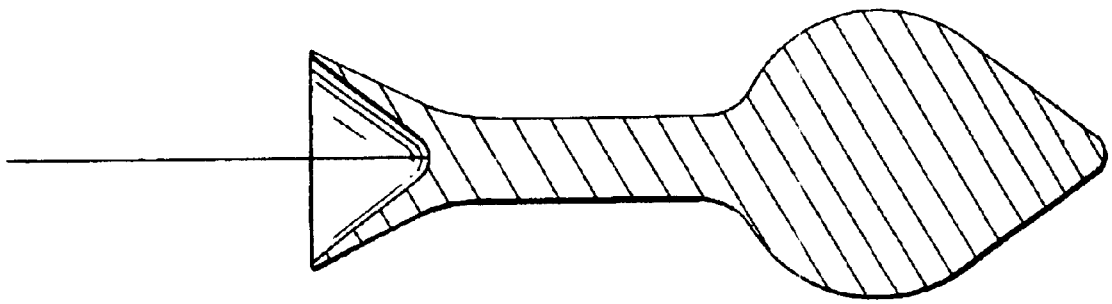
Figure 8:
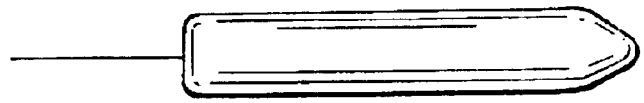
FIG. 8. Example of suitable shape of a rectal suppository
Figure 9A:
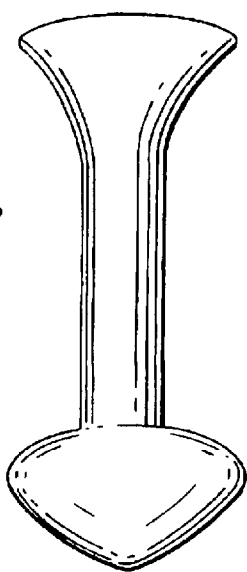
FIGS. 9a, 9b, 9c, 9d, 9e and 9f illustrate examples of suitable shapes of rectal suppositories.
Figure 9D:
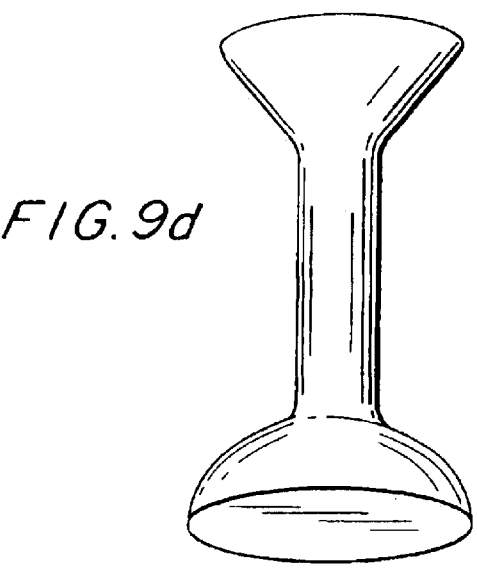
Figure 9B:
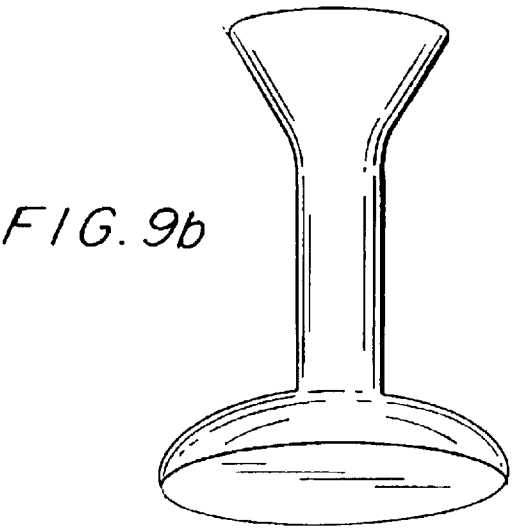
Figure 9E:
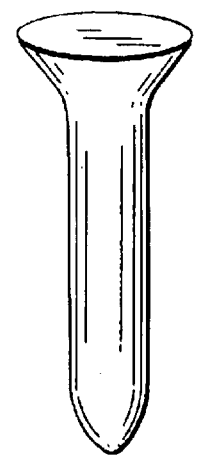
Figure 9C:
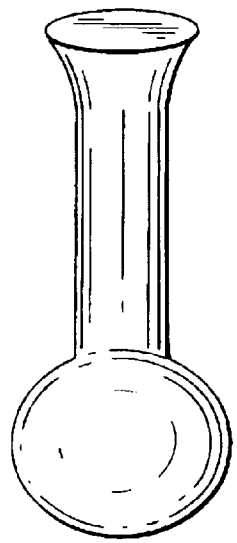
Figure 9F:
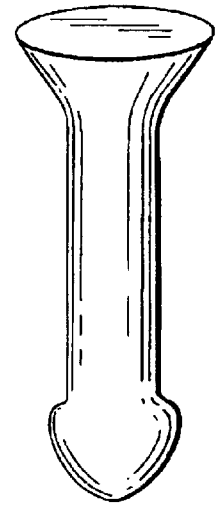

The shape of the flange makes it possible to administer medicaments for treatment of hemoroids located at the entry to the rectum, or any or pains associated with such hemoroids. This principle is illustrated in FIG. 6 showing the approximate location of a rectal suppository (black object) in the rectum.

Other embodiments of suppositories according to the invention have an overall axial length of between 1.0 cm and about 10 cm, preferably between 2.0 cm and 7.5 cm, such as e.g. between 3.0 cm and 7.5 cm, for example between 4.0 cm and 7.5 cm, such as about 7.5 cm.

The axial length of the central part of the suppository is preferably between 0.5 and 7.5 cm, and preferably between 2.0 and 6.5 cm, such as e.g. between 2.5 cm and 6.0 cm, for example between 3.0 cm and 5.0 cm, such as about 4.5 cm.

Figure 3A:
FIG. 3. Example of suitable shape of a suppository for use in the ear.
Figure 3B:
Figure 4A:
FIG. 4. Example of suitable shape of a nasal suppository
Figure 4B:
Figure 5:
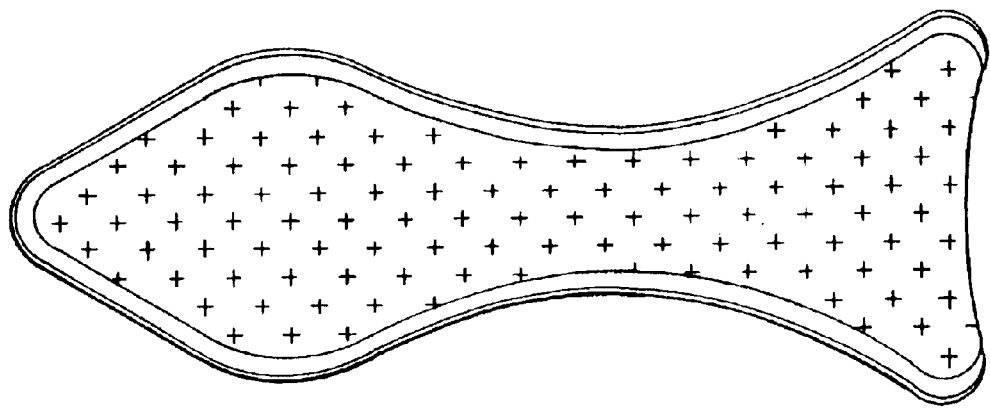
FIG. 5. Example of suitable shape of a rectal suppository

A suppository according to the present invention is capable for use either as a rectal suppository (one preferred embodiments shown in FIGS. 1, 5 and 6), a vaginal suppository (one preferred embodiment shown in FIG. 2), an otogenic suppository for use in the ear (one preferred embodiment shown in FIG. 3), and a nasal suppository (one preferred embodiment shown in FIG. 4).

Figures 2A, 2B:
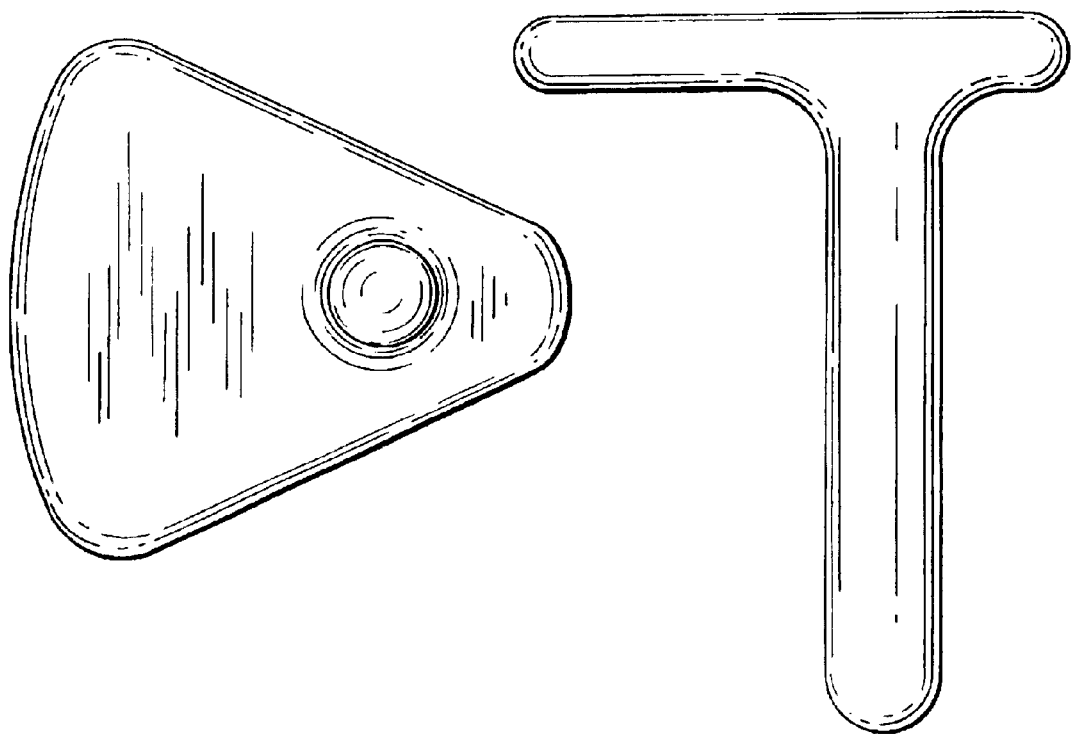
FIG. 2. Example of suitable shape of a vaginal suppository

A suppository designed for use as a vaginal suppository is shown in FIG. 2 illustrating a frontal view of a flange portion in a triangular shape (A) with the dimensions of about 7 cm times about 7 cm, Part (B) of the figure shows a side view of the suppository, wherein the flange portion is attached to the proximal end of a central portion with an average diameter of about 1.2 cm to 1.8 cm, preferably a uniform diameter of about 1.5 cm, and a distal end portion having a rounded tip.

A suppository designed for use in the ear is illustrated in FIG. 3 showing a side view (A) dislosing a flange portion and a central portion having a uniform diameter of about 0.7 cm to 0.9 cm, and a rounded distal end portion. The overall length of the suppository is about 2.5 cm to about 3.0 cm, preferably about 2.8 cm. Part (B) is a frontal view illustrating a circularly shaped flange portion with a diameter of about 0.8 cm to 1.2 cm.

FIG. 4 shows a conically shaped nasal suppository with an overall length of about 1.8 cm to 2.2 cm, preferably about 2.0 cm, and a maximum diameter of about 0.8 cm to 1.2 cm, preferably about 1.0 cm.

EXAMPLES

The below mentioned examples do exemplify specific embodiments of the invention and should not be regarded as limiting for the invention.

Example 1

Polymer Compositions
Materials
Polyols
Arcol 1025 (ARCO Chemical Products Europe Inc.). Long chained diol based on 2.2-dihydroxydipropylether with an OH-value of 9 mg KOH/g
Arcol 320 (ARCO Chemical Products Europe Inc.). Low Molecular weight polyoxypropylene triol with an OH-value of 381 mg KOH/g
Isocyanate
Lupranat M20S (BASF Elastogran)
Diphenylmethandiisocyanate (MDI) with NCO-%=30%
Others
Tegostab B 8229 (Th Goldschmidt)
Siliconoil—cell regulating/cell opening
Tegostab B 8694 (Th Goldschmidt)
Tegostab B 8729LF (Th Goldschmidt)
Tegostab B 8715LF(Th Goldschmidt)
Baylith L Paste (Bayer AG)
Zeolith suspended in oil—water aborbant
CTX-20101 (ChemTrend A/S)
Linen
Catalyst
DABCO 33 LV (Edulan A/S)
33% triethylene diamine dissolved in dipropyleneglycol
Mixtures

| A: | |
|---|---|
| Arcol 1025 | 100 weight units |
| H2O | 2 weight units |
| Tegostab B8229 | 2 weight units |
| DABCO 33 LV | 1 weight units |
| Lupranat M20S | 44 weight units |
| Density. 1200 g/l | |
| B: | |
| Arcol 1025 | 80 weight units |
| Arcol 3320 | 20 weight units |
| Baylith L Paste | 5 weight units |
| DABCO 33 LV | 1 weight units |
| Lupranat M20S | 29 weight units |
| Density 90 to 200 g/l | |
| 100% open cells | |
| C: | |
| Arcol 1025 | 10 weight units |
| H$_2$O | 0.2 weight units |
| Tegostab B8694 | 0.4 weight units |
| DABCO 33 LV | 0.1 weight units |
| Lupranat M20S | 4.4 weight units |
| D: | |
| Arcol 1025 | 10 weight units |
| H$_2$O | 0.2 weight units |
| Tegostab B8694 | 0.2 weight units |
| DABCO 33 LV | 0.1 weight units |
| Lupranat M20S | 4.4 weight units |
| E: | |
| Arcol 1025 | 10 weight units |
| H$_2$O | 0.2 weight units |
| Tegostab B8729LF | 0.2 weight units |
| DABCO 33 LV | 0.1 weight units |
| Lupranat M20S | 4.4 weight units |
| F: | |
| Arcol 1025 | 10 weight units |
| H$_2$O | 0.2 weight units |
| Tegostab B8715LF | 0.2 weight units |
| DABCO 33 LV | 0.1 weight units |
| Lupranat M20S | 4.4 weight units |

Example 2

Controlled Release Formulations
Materials
Polyethylene glycol (PEG)
8000 Hoechst
4000 Hoechst; Clariant
1500 Hoechst
400 Merck Schuchart; Clariant
10,000 Merck Schuchart
6000 Merck Schuchart; Clariant
35,000 Clariant
3500 Clariant
2000 Clariant
1000 Unikem-Macrogol; Clariant

| Mixtures: | | | |
|---|---|---|---|
| G: | | | |
| PEG 1500 | PEG 400 | | 95:5 |
| H: | | | |
| PEG 2000 | PEG 1500 | | 1:3 |
| I: | | | |
| PEG 2000 | PEG 1000 | | 1:1 |
| J: | | | |
| PEG 4000 | PEG 1000 | | 1:3 |
| K: | | | |
| PEG 4000 | PEG 1000 | | 4:96 |
| L: | | | |
| PEG 4000 | PEG 1000 | PEG 400 | 6:3:1 |

Example 3

Controlled Release Formulations Comprising a Bioactive Substance
Materials
PEG see example 2
Caffeine ph.Eur.srdEd (Unikem, cat.no. 264283)
Mixture
M:
PEG 4000 and PEG 1000
Mixed at a ratio of 1:3
0.45% caffeine

What is claimed is:

1. Suppository for administration of at least one bioactive substance, said suppository comprising
   i) a polymer composition comprising at least one biocompatible polymer, wherein the biocompatible polymer is essentially non-biodegradable; and
   ii) a controlled release formulation for controlled release of said at least one bioactive substance, said formulation comprising at least one biodegradable polymer; and
   wherein the suppository essentially does not swell when contacted with an aqueous fluid.

2. The suppository according to claim 1, wherein the polymer compositions has a density of from about 100 gram per litre to about 250 gram per litre.

3. The suppository according to claim 1, wherein the compression modulus of the polymer composition at ambient temperature is from about 10 kPa to about 30 kPa.

4. The suppository according to claim 1, wherein the polymer composition further comprises a mixture of cells selected from the group consisting of open cells and closed cells.

5. The suppository according to claim 4, wherein the majority of the cells are open cells.

6. The suppository according to claim 5, wherein more than about 90% of the cells are open cells.

7. The suppository according to claim 6, wherein essentially all the cells are open cells.

8. The suppository according to claim 1, wherein the polymer composition further comprises a plurality of open cells at least partly separated from one another by an interpenetrating matrix comprising at least one biocompatible polymer in branched or crosslinked form.

9. The suppository according to claim 8, wherein at least part of the polymer composition comprises a plurality of interlinked, open cells capable of containing an aqueous fluid.

10. The suppository according to claim 9, wherein the contacting of the suppository with an aqueous fluid under practical circumstances results in essentially no fluid entering the open cells.

11. The suppository according to claim 10, wherein the permeability of the polymer composition results in entry of fluid into the open cells under practical circumstances essentially without dehydration of mucousal membrane tissue contacting the suppository.

12. The suppository according to claim 1, wherein the glass-rubber transition temperature of the polymer of the polymer composition is above about 15° C. and preferably below 40° C., such as a glass rubber transition temperature in the range of about 20° C. to about 40° C., for example about 35° C., such as about 36° C., for example in the range of about 25° C. to about 35° C., such as in the range of about 30° C. to about 35° C.

13. The suppository according to claim 1, wherein the biocompatible polymer is selected from the group consisting of polyurethanes, polyethylenes, and polypropylenes.

14. The suppository according to claim 1, wherein the biocompatible polymer is a polyurethane.

15. The suppository according to claim 14, wherein the polyurethane comprises at least one polyisocyanat that is at least partly polymerised with at least one polyol.

16. The suppository according to claim 15, wherein essentially all of the at least one polyisocyanat is polymerised with essentially all of the at least one polyol.

17. The suppository according to claim 15, wherein the at least one polyisocyanat is selected from the group consisting of aromatic polyisocyanates, aliphatic polyisocyanates, and heterocyclic polyisocyanates.

18. The suppository according to claim 15, wherein the at least one polyol is selected from the group consisting of aromatic polyols, aliphatic polyols, and heterocyclic polyols.

19. The suppository according to claim 15, wherein the at least one polyol is aliphatic and the at least one polyisocyanat is aliphatic.

20. The suppository according to claim 15, wherein the at least one polyol is aliphatic, such as a polymer comprising or essentially consisting of 2,2-dihydroxy-dipropylether, and the at least one polyisocyanat is aromatic, such as a polymer comprising or essentially consisting of diphenylmethandiisocyanat.

21. The suppository according to claim 15, wherein the at least one polyol is aromatic and the at least one polyisocyanat is aliphatic.

22. The suppository according to claim 15, wherein the at least one polyol is aromatic and the at least one polyisocyanat is aromatic.

23. The suppository according to claim 15, comprising two polyols.

24. The suppository according to claim 15, wherein the polyol is selected from the group consisting of diols and triols.

25. The suppository according to claim 23, wherein the average functionality of the at least one polyol is between 0.2 and 5, preferably between 0.5 and 2.

26. The suppository according to claim 15, wherein the ratio of i) NCO groups contained in the at least one polyisocyanate to ii) OH groups contained in the at least one polyol, respectively, is within the range of from about 0.5 to about 2.5, and preferably within the range of about 0.7 to about 1.3.

27. The suppository according to claim 1, wherein the controlled release formulation has a softening point between 15° C. and 45° C.

28. The suppository according to claim 1, wherein the controlled release formulation has a softening point between 25° C. and 40° C.

29. The suppository according to claim 1, wherein the controlled release formulation has a softening point between 30° C. and 35° C.

30. The suppository according to claim 1, wherein the controlled release formulation has a softening point such as the suppository is essentially rigid at room temperature, and the suppository is essentially soft at body temperature.

31. The suppository according to claim 1, wherein the controlled release formulation comprises two different biodegradable polymers.

32. The suppository according to claim 1, wherein the controlled release formulation comprises more than two different biodegradable polymers.

33. The suppository according to claim 1, wherein at least one polymer of the controlled release formulation is selected from the group consisting of polyethyleneglycols (PEG).

34. The suppository according to claim 33, wherein the PEG has an average molecular weight of between 100 and 1500.

35. The suppository according to claim 33, wherein the PEG has an average molecular weight of between 400 and 1000.

36. The suppository according to claim 33, wherein the PEG has an average molecular weight of around 400.

37. The suppository according to claim 33, wherein the PEG has an average molecular weight of around 1000.

38. The suppository according to claim 33, wherein the PEG has an average molecular weight of more than 1000.

39. The suppository according to claim 33, wherein the PEG has an average molecular weight between 1000 and 35,000.

40. The suppository according to claim 33, wherein the PEG has an average molecular weight between 1500 and 10,000.

41. The suppository according to claim 33, wherein the PEG has an average molecular weight around 2000.

42. The suppository according to claim 33, wherein the PEG has an average molecular weight around 4000.

43. The suppository according to claim 33, wherein the PEG has an average molecular weight 6000.

44. The suppository according to claim 31, wherein the controlled release formulation comprises (1) a polymer which is selected from the group consisting of PEG with an average molecular weight of between 200 and 1500 and (2) a polymer which is selected from the group consisting of PEG with an average molecular weight of between 1000 and 35,000.

45. The suppository according to claim 44, wherein the polymer (1) is PEG with an average molecular weight around 1000 and the polymer (2) is PEG with an average molecular weight around 4000.

46. The suppository according to claim 1, wherein the controlled release formulation furthermore comprises a surface active agent.

47. The suppository according to claim 1, wherein the surface active agent is a PEG monoester.

48. The suppository according to claim 1, wherein the surface active agent is a PEG monostearate.

49. The suppository according to claim 1, wherein the suppository comprises a central core comprising a first composition, and a surrounding part surrounding the central core and comprising a second composition.

50. The suppository according to claim 49, wherein the central core comprises the controlled release formulation and the surrounding part comprises the polymer composition.

51. The suppository according to claim 49, wherein the density of the central core, measured as mass per unit volume, is higher than the density of the surrounding part, measured as mass per unit volume.

52. The suppository according to claim 49, that further comprises a peripheral part comprising a third composition that is not identical to any of said first and second compositions, and wherein at least part of the third composition is in contact with the surrounding part comprising the second composition.

53. The suppository according to claim 52, wherein said peripheral part is a layer controlling the water permeability of the suppository by defining a barrier between the suppository and fluid present in an external environment that is in contact with the suppository under practical circumstances.

54. The suppository according to claim 1 and further comprising a coating composition, wherein the coating composition covers at least part of the surface area of said suppository, and wherein the coating composition is not identical to the polymer.

55. The suppository according to claim 1, wherein the bioactive substance is a medicament.

56. The suppository according to claim 55, wherein the medicament is selected from the group consisting of analgetics.

57. The suppository according to claim 56, wherein the analgetic is lidocain.

58. The suppository according to claim 1, wherein the controlled release formulation comprises the bioreactive substance comprised in capsules comprising at least one encapsulation agent.

59. The suppository according to claim 56, wherein the capsules comprise an encapsulation agent selected from the group of encapsulation agents consisting of PEG, proteins, lipids, and casein.

60. The suppository according to claim 56, wherein the capsules are adapted to disintegrate and release the medicament when contracting body tissue.

61. The suppository according to claim 56, wherein the capsules comprising the medicament are adapted to disintegrate and release the medicament when contacting a fluid, including moisture secreted by body tissue.

62. The suppository according to claim 56, wherein the capsules are adapted to dissolve and release the medicament when contacting body tissue.

63. The suppository according to claim 56, wherein the capsules comprising the medicament are adapted to dissolve and release the medicament when contacting a fluid.

64. The suppository according to claim 1, that further comprises an additive selected from the group of preservatives, adjuvants, stabilizers, lubricants, and disintegraters or any combinations thereof.

65. The suppository according to claim 1, wherein the suppository has an essentially oblong shape.

66. The suppository according to claim 1, wherein the suppository has an essentially cylindrical shape.

67. The suppository according to claim 1, wherein the suppository has a central portion, a first end portion and a second end portion, wherein at least one of said end portions is tapering, and preferably pointed.

68. The suppository according to claim 1, wherein the suppository has a central portion, a tapering, distal end portion, and a proximal end portion attached to a flange portion extending outwardly in the axial direction from said proximal end portion.

69. The suppository according to claim 67, wherein said flange portion has a recessed part in the axial direction.

70. The suppository according to claim 69, wherein the suppository has a shape that allows contact between parts of or essentially all of the outer surface of the suppository and parts of or essentially all of the mucosal membrane of the rectum below the caudal semilunary fold, when the suppository is situated in the rectum.

71. Method for preparation of a suppository according to claim 1, said method comprising the steps of
   i) providing at least one monomeric reagent suitable for polymerization,
   ii) polymerising said at least one monomeric reagent and obtaining a biocompatible polymer which is essentially non-biodegradable,
   iii) providing a controlled release formulation for controlled release of at least one bioactive substance,
   iv) mixing the controlled release formulation and the at least one bioactive substance, and
   v) shaping the essentially non-biodegradable, biocompatible polymer and the mixture of the controlled release formulation and the at least one bioactive substance into a shape desirable for a suppository.

72. Method according to claim 71, wherein the suppository is shaped by injection moulding into a predetermined shape.

73. Method of claim 71, wherein the monomeric reagents used for obtaining the essentially non-biodegradable, biocompatible polymer comprise at least one polyisocyanate and at least one polyo.

74. Suppository obtainable by the method of claim 71.

75. Method for alleviating pain in an individual in need thereof, said method comprising the steps of contacting body tissue of a body cavity of the individual with the suppository of claim 1, wherein the suppository comprises the bioactive substance in an amount effective to achieve said pain alleviation in said individual.

76. A method for diagnosing a clinical indication in an individual comprising the steps of bringing a suppository according to claim 1 into contact with body tissue of a body cavity an animal, wherein the suppository comprises a diagnostically active substance in an amount effective to achieve said diagnosis.

77. A cosmetic method comprising the steps of bringing a suppository according to claim 1 into contact with body tissue of a body cavity of an animal, wherein the suppository comprises a cosmetically active substance in an amount sufficient to achieve a desirable cosmetic effect.

78. The suppository of claim 33, where the controlled release formulation comprises
    (a) a biodegradable polyethylene glycol with a molecular weight of between 100 and 1500, and
    (b) a biodegradable polyethylene glycol with a molecular weight of between 1500 and 10,000.

79. The suppository of claim 33, where the controlled release formulation comprises
    (a) a biodegradable polyethylene glycol with a molecular weight of between 400 and 1000, and
    (b) a biodegradable polyethylene glycol with a molecular weight of more than 1000.

80. The suppository of claim 79 where PEG (b) has a molecular weight of not more than 35,000.

81. The suppository of claim 33 where at least two of the biodegradable polymers of said controlled release formulation differ in melting point from each other.

82. The suppository of claim 81 where the ratio of the lowest melting point biodegradable polymer to the highest melting point polymer of said controlled release formulation is about 3:1.

83. Method of claim 75, wherein the bioactive substance is selected from the group consisting of analgesics, anaesthetics and antipyretics.

84. Method of claim 75, wherein the bioactive substance is selected from opioid analgesics, non-opioid analgesics, and lidocaine, and antiepileptics used to alleviate pain.

85. Method of claim 75, wherein the bioactive substance is selected from lidocaine, codeine, morphine, acetaminophen, aspirin, and ibuprofen.

86. Method of claim 75, wherein the body tissue is a rnucosal surface.

87. Method of claim 86, wherein the mucosal surface is a mucosal surface of the rectum.

88. Method of claim 87, wherein the mucosal surface of the rectum is the surface located below the caudal semilunary fold.

89. Method of claim 75, wherein the individual is a human being.

90. In a method for surgical treatment of ruptured colon in an individual, the improvement comprising alleviating pain by performing the steps of contacting body tissue of a body cavity of the individual with the suppository of claim 1, wherein the suppository comprises an analgesic bioactive substance or an anaesthetic bioactive substance in an amount effective to achieve said pain alleviation in said individual.

91. Method of claim 90, wherein the body tissue is a mucosal surface.

92. Method of claim 91, wherein the mucosal surface is a mucosal surface of the rectum.

93. Method of claim 92, wherein the mucosal surface of the rectum is the surface located below the caudal semilunary fold.

94. Method of claim 90, wherein the individual is a human being.

95. In a method for rectal surgery performed on an individual, the improvement comprising alleviating pain by performing the steps of contacting body tissue of a body cavity of the individual with the suppository of claim 1, wherein the suppository comprises an analgesic bioactive substance or an anaesthetic bioactive substance in an amount effective to achieve said pain alleviation in said individual.

96. Method of claim 95, wherein the body tissue is a mucosal surface.

97. Method of claim 96, wherein the mucosal surface is a mucosal surface of the rectum.

98. Method of claim 97, wherein the mucosal surface of the rectum is the surface located below the caudal semilunary fold.

99. Method of claim 95, wherein the individual is a human being.

100. In a method for surgical treatment of haemorrhoids in an individual, the improvement comprising alleviating pain by performing the steps of contacting body tissue of a body cavity of the individual with the suppository of claim 1, wherein the suppository comprises an analgetic bioactive substance or an anaesthetic bioactive substance in an amount effective to achieve said pain alleviation in said individual.

101. Method of claim 100, wherein the body tissue is a mucosal surface.

102. Method of claim 101, wherein the mucosal surface is a mucosal surface of the rectum.

103. Method of claim 102, wherein the mucosal surface of the rectum is the surface located below the caudal semilunary fold.

104. Method of claim 100, wherein the individual is a human being.

105. In a method for surgical treatment of ruptured vagina of a female mammal, the improvement comprising alleviating pain by performing the steps of contacting a mucosal surface of the vagina of the female mammal with the suppository of claim 1, wherein the suppository comprises an analgetic bioactive substance or an anaesthetic bioactive substance in an amount effective to achieve said pain alleviation in said female mammal.

106. Method of claim 105, wherein the mammal is a human being.

107. A method for treating an inflammatory condition in an individual, said method comprising the steps of contacting body tissue of a body cavity of the individual with the suppository of claim 1, wherein the suppository comprises an anti-inflammatory bioactive substance in an amount effective in treating said inflammatory condition.

108. Method of claim 107, wherein the body tissue is a mucosal surface.

109. Method of claim 108, wherein the mucosal surface is a mucosal surface of the rectum.

110. Method of claim 109, wherein the mucosal surface of the rectum is the surface located below the caudal semilunary fold.

111. Method of claim 107, wherein the individual is a human being.

112. Method of claim 107, wherein the anti-inflammatory bioactive substance is selected from the group consisting of naproxyn, diclofenac, indomethacin, ibuprofen, acetaminophen, aspirin, and sulindac.

113. Method of claim 107, wherein the anti-inflammatory bioactive substance is selected from the group consisting of hydrocortisone, triamcinolone, prednisone, cortisone acetate, prednisolone, methyl prednisolone and dexamethasone.

114. Method for treating an infection in an individual, said method comprising the steps of contacting body tissue of a body cavity of the individual with the suppository of claim 1, wherein the suppository comprises an anti-infective bioactive substance in an amount effective in treating said infection.

115. Method of claim 114, wherein the body tissue is a mucosal surface.

116. Method of claim 115, wherein the mucosal surface is a mucosal surface of the rectum.

117. Method of claim 116, wherein the mucosal surface of the rectum is the surface located below the caudal semilunary fold.

118. Method of claim 114, wherein the individual is a human being.

119. Method of claim 114, wherein the anti-infective bioactive substance is selected from the group consisting of anti-biotics, anti-fungals, anti-virals, and anti-septics and anti-protozoans.

120. Method of claim 114, wherein the anti-biotic is selected from the group consisting of penicillins, cephalosporins, tetracyclines, ampicillin, aureothicin, bacitracin, chioramphenicol, cycloserine, erythromycin, gentamicin, gramacidin, kanamycin, neomycin, streptomycin, tobramycin, vancomycin, and metronidazole.

121. Method of claim 114, wherein the anti-biotic is a beta-lactam antibiotic selected from the group consisting of sulbenicillin, mecillinam, carbenicillin, piperacillin, ticarcillin, and thienamycin.

122. Method of claim 114, wherein the anti-biotic is a cephalosporin selected from the group consisting of cefotiam, cefsulodine, cefmenoxime, cefmetazole, cefazolin, cefotaxime, cefoperazone, ceftizoxime and moxalactam.

123. Method of claim 114, wherein the anti-viral bioactive species is acyclovir.

124. A method for treating a cancer in an individual, said method comprising the steps of contacting body tissue of a body cavity of the individual with the suppository of claim 1, wherein the suppository comprises an anti-cancer bioactive substance in an amount effective in treating said cancer.

125. Method of claim 124, wherein the body tissue is a mucosal surface.

126. Method of claim 125, wherein the mucosal surface is a mucosal surface of the rectum.

127. Method of claim 126, wherein the mucosal surface of the rectum is the surface located below the caudal semilunary fold.

128. Method of claim 124, wherein the individual is a human being.

129. Method of claim 124, wherein the anti-cancer bioactive substance is selected from the group consisting of antimetabolites, cytotoxic agents and immunomodulators.

130. Method of claim 129, wherein the antimetabolites are selected from methotrexate, 5-fluorouracil, cytosine arabinoside(ara-C), 5-azacytidine, 6-mercaptopurine, 6-thioguanine, and fludarabine phosphate.

131. Method of claim 129, wherein the cytotoxic agents are selected from taxol, epirubicin, esorubicin, doxorubicin, iodo-doxorubicin, daunorubicin, idarubicin, dactinomycin, bleomycin, mitomycin C, plicamycin, mitoxantrone, vincristine, vinblastine, vindesine, etoposide, and teniposide.

132. Method of claim 124, wherein the anti-cancer bioactive substance is selected from the group consisting of 5'-fluorouracil, mitomycin, cisplatin, taxol, biteomycins, daunomycins, and methamycins.

133. Method for treating a hormone condition in an individual, said method comprising the steps of contacting body tissue of a body cavity of the individual with the suppository of claim 1, wherein the suppository comprises a hormone bioactive substance in an amount effective in treating said deficiency.

134. Method of claim 133, wherein the body tissue is a mucosal surface.

135. Method of claim 134, wherein the mucosal surface is a mucosal surface of the rectum.

136. Method of claim 135, wherein the mucosal surface of the rectum is the surface located below the caudal semilunary fold.

137. Method of claim 133, wherein the individual is a human being.

138. Method of claim 133, wherein the hormone is selected from growth hormone, tPA (tissue plasminogen activator), prolactin, adrenocorticotrophic hormone, melanocyte stimulating hormone, thyrotropin releasing hormone, thyroid stimulating hormone, thyroxine, luteinizing hormone, follicle stimulating hormone, vasopressin, oxytocin, calcitonin, parathyroid hormone, glucagon, gastrin, secretin, pancreozymin, cholecystokinin, angiotensin, human placental lactogen, human chorionic gonadotropin, enkephalin, endorphin, insulin, alpha interferon, beta interferon, and gamma interferon.

139. Method of claim 133, wherein the hormone is selected from corticosteriods, estrogens, progestins, antiestrogens, aromastase inhibitors, androgens, antiandrogens, and endocrines for prostate cancer.

140. Method of claim 133, wherein the hormone is selected from cortisone acetate, hydrocortisone, prednisone, prednisolone, methyl prednisolone and dexamethasone, diethyistibesterol, estradiol, esterified estrogens, conjugated estrogen, chiorotiasnene, medroxyprogesterone acetate, hydroxy progesterone caproate, megestrol acetate, tamoxifen, aminoglutethimide, testosterone propionate, methyltestosterone, fluoxymesterone, testolactone, flutamide, leuprolide acetate, and ketoconazole.

141. A method for contraception comprising the steps of contacting body tissue of a body cavity of a female mammal with the suppository of claim 1, wherein the suppository comprises a contraceptive bioactive substance in an amount effective to achieve said contraception in said female mammal.

142. Method of claim 141, wherein the body tissue is a mucosal surface.

143. Method of claim 142, wherein the mucosal surface is a mucosal surface of the vagina.

144. Method of claim 141, wherein the mammal is a human being.

145. A surgical method performed on an individual, comprising modifying blood coagulation by performing the steps of contacting body tissue of a body cavity of the individual with the suppository of claim 1, wherein the suppository comprises a coagulation modifying agent in an amount effective to achieve said blood coagulation modification.

146. Method of claim 145, wherein the body tissue is a mucosal surface.

147. Method of claim 146, wherein the mucosal surface is a mucosal surface of the rectum.

148. Method of claim 147, wherein the mucosal surface of the rectum is the surface located below the caudal semilunary fold.

149. Method of claim 145, wherein the individual is a human being.

150. Method for immunising an individual, said method comprising the steps of contacting body tissue of a body cavity of the individual with the suppository of claim 1, wherein the suppository comprises an antigenic substance in an amount effective in achieving said immunisation.

151. Method of claim 150, wherein the body tissue is a mucosal surface.

152. Method of claim 151, wherein the mucosal surface is a mucosal surface of the rectum.

153. Method of claim 152, wherein the mucosal surface of the rectum is the surface located below the caudal semilunary fold.

154. Method of claim 150, wherein the individual is a human being.

155. Method of claim 150, wherein the suppository further comprises an adjuvant.

* * * * *